United States Patent [19]

Cho

[11] Patent Number: 5,366,665
[45] Date of Patent: Nov. 22, 1994

[54] COMPOSITIONS COMPRISING ALKYL SULFOOXYALKANOATE COMPOUNDS CONTAINING A BENEFICIAL REAGENT COMPONENT

[75] Inventor: Suk H. Cho, Teaneck, N.J.

[73] Assignee: Lever Brothers Company, Division of Conopco, Inc., New York, N.Y.

[21] Appl. No.: 28,500

[22] Filed: Mar. 9, 1993

Related U.S. Application Data

[63] Continuation-in-part of Ser. No. 738,082, Jul. 30, 1991, abandoned.

[51] Int. Cl.$^5$ ............................................. C11D 1/12
[52] U.S. Cl. .................................. 252/549; 252/550; 252/DIG. 5; 424/65; 424/70; 514/844; 558/32; 558/38; 554/97
[58] Field of Search .................. 252/549, 550, DIG. 5; 424/65, 70; 514/844; 558/32, 38; 554/97

[56] References Cited

U.S. PATENT DOCUMENTS

| | | | |
|---|---|---|---|
| 2,107,197 | 4/1935 | Butignot | 558/32 |
| 2,225,673 | 12/1940 | Werntz | 558/32 |
| 2,285,773 | 6/1942 | Harris | 558/32 |
| 2,402,823 | 4/1943 | Kyrides | 564/471 |
| 3,595,903 | 7/1971 | Peco | 558/32 |
| 3,948,818 | 4/1976 | Tomiyama et al. | 252/542 |
| 4,197,316 | 4/1980 | Yu et al. | 424/317 |
| 4,294,852 | 10/1981 | Wildnauer et al. | 424/317 |
| 4,507,319 | 3/1985 | Barratt et al. | 514/546 |
| 4,530,726 | 7/1985 | Montiel | 252/555 |
| 4,692,261 | 9/1987 | Filomeno | 252/551 |
| 4,891,143 | 1/1990 | Woodward et al. | 252/8.75 |
| 5,114,706 | 5/1992 | Duvel | 424/70 |

FOREIGN PATENT DOCUMENTS

91/11504  8/1991  WIPO .

OTHER PUBLICATIONS

Chemical Abstract No. 87381d vol. 73, No. 17 (Kiik), Oct. 26, 1970.
European Search Report & Annex.
Feete, Seifen, Anstrichmittel 67(9):677-682 (1965).
Chemical Abstract No. 117596d, vol. 83, No. 14 (1965).
Chemical Abstract No. 137823b, vol. 95, No. 16 May (1981).
Chemical Abstract No. 196611f, vol. 116, No. 20.
Pelisha et al., Biochemistry, 28(4):1604-1612, Feb. (1989).
Chemical Abstract No. 7502e, vol. 113,, No. 2 (1990).
Chemical Abstract No. 128595t, vol. 107, No. 15 (1987).
Chemical Abstract No. 2394e, vol. 102, No. 1 (1985).
Chemical Abstract No. 204670m, vol. 100, No. 25 (1984).
Chemical Abstract No. 72609x, vol. 99, No. 10 (1983).
Chemical Abstract No. 36661n, vol. 96, No. 6 (1982).
Chemical Abstract No. 21647y, vol. 88, No. 3 (1977).
Chemical Abstract No. 151061x, vol. 36, No. 21 (1977).
Chemical Abstract No. 7909p, vol. 80, No. 15 (1974).
Chemical Abstract No. 16323v, vol. 80, No. 4 (1974).
Chemical Abstract No. 74447a, vol. 74, No. 15 (1971).
Chemical Abstract No. 55902w, vol. 70, No. 13 (1969).
Peliska et al., Biochemistry, 28:1604-1611 (1989).
Caryl, C. R. Industrial and Engineering Chemistry 33(6):731 (1941).
Stirton et al, Journal of American Oil Chemists' Society, 39:490 (1962).
Smith et al., Journal of American Chemistry Society 44:405 (1967).
Hikota et al., Journal of American Oil Chemists' Society, 47:158 (1970).
Hikota et al., Bulletin of the Chemical Society of Taipan, 43:3913 (1970).
Schuelke, CA 113(7):58069(c) (Abstract) (1989).
Zabran et al., Khim. Volokna, 14(2):33-4 (Abstract).
Fabry, CA116(12):108835d Aug. (1991).

Primary Examiner—Paul Lieberman
Assistant Examiner—Necholus Ogden
Attorney, Agent, or Firm—Ronald A. Koatz

[57] ABSTRACT

The present invention relates to personal product compositions selected from the group consisting of soap bar compositions, facial or body cleansing compositions, shampoo compositions, conditioner compositions, cosmetic compositions, dental compositions, and underarm deodorant/anti-perspirant compositions comprising specific alkyl sulfooxy alkanoate surfactant compounds. A portion of the alkyl sulfooxy alkanoate surfactants contains a "benefit reagent" which forms when the molecule is metabolized by enzymes on the body or elsewhere or which forms when the surfactant spontaneously hydrolyses on the skin surface.

4 Claims, No Drawings

COMPOSITIONS COMPRISING ALKYL SULFOOXYALKANOATE COMPOUNDS CONTAINING A BENEFICIAL REAGENT COMPONENT

CROSS REFERENCES

This application is a continuation-in-part of U.S. Ser. No. 07/738,082, filed Jul. 30, 1991, abandoned.

BACKGROUND OF THE INVENTION

1. Field of the Invention

This invention relates to novel personal product compositions as well as to alkyl sulfooxyalkanoate surfactants used in the compositions and methods for the preparation of these surfactants. A portion of the surfactant molecule functions as a so-called "benefit reagent" which will form when the molecule is metabolized by enzymes present in the body or elsewhere or which will form when the molecule spontaneously hydrolyzes on the skin surface. Personal products compositions comprising these sulfooxyalkanoate compounds include hair/body shampoos, cleansing creams, conditioners, cosmetic applications, dental applications, underarm deodorant/antiperspirant applications and sunblock applications. Other applications include soaps, powders, lotions and therapeutic creams. This list is not intended to be exhaustive and other compositions in which surfactants may be used are also contemplated.

2. Prior Art

In the past decades, "mildness" has become an increasingly important criterion in selecting surfactants for personal products. The term "mildness" means that surfactants do not produce any skin irritation. Many consumers recognize the skin damaging effects surfactants may have. Therefore, a surfactant used for personal products should not only possess good surface active properties, but should also be safe on human skin.

Although many factors, e.g., removal of skin lipids, loss of naturally occurring hygroscopic materials in the stratum corneum, adsorption, protein denaturation, epidermal liposomal injury, are known to have an influence on skin irritation, it is generally believed that surfactants cause skin irritation by penetrating the stratum corneum and reacting with the inner cells of the epidermis. Accordingly, one approach to achieving "mildness" is to prevent surfactants from penetrating the stratum corneum and reacting with those cells.

A second approach for obtaining "mildness" is to design surfactants which can penetrate the stratum corneum but which, once they have penetrated, degrade to harmless components, possibly with the aid of enzymes. This second approach (the approach followed by the subject invention) attempts to take advantage of the enzymatic activity which is believed to be present in the sublayer of the stratum corneum. See Foster et al, Arch Derm. Res., 25:23-28 (1975) and Kermici et al, J. Soc. Cosmet Chem., 28:151-164 (1977).

It is also known in the art that hydroxy acids have beneficial effects on the skin. U.S. Pat. No. 4,197,316 to Yu et al. for example, discloses a non-irritating therapeutic composition for alleviating dry skin symptoms wherein the composition contains hydroxy acids (e.g., $\alpha$-hydroxy butyric acid, lactic acid and citric acid). U.S. Pat. No. 4,294,852 to Widnaer et al. teaches skin treating compositions comprising hydroxy acids. U.S. Pat. No. 4,507,319 to Barret et al. also describes skin treatment compositions possessing $\alpha$-hydroxy octanoate acid.

None of these patents teach a surfactant material which is able to deliver the hydroxy acid component to the skin.

Accordingly, it would be particularly beneficial to design compositions comprising a surfactant molecule wherein the surfactant not only breaks down inside the skin or which spontaneously hydrolyzes upon contact with the skin surface, but to design a molecule which, one it has been broken down in the skin or once it has hydrolyzed, will have a beneficial effect on (e.g., alleviating dryness, imparting antimicrobial activity, etc.) or will deliver a benefit to the skin.

In U.S. patent application No. 628,243, filed Dec. 17, 1990 and hereby incorporated by reference, the inventor of the subject application provides novel compositions comprising phosphate esters which are designed to break down or hydrolyze and to impart the beneficial reagent component described above. There is no description of compositions comprising the sulfooxy analogs of the present invention in that disclosure.

Peliska et al. in Biochemistry, 28: 1604-11 (1989), disclose simple sulfoenol pyruvate compounds prepared in order to study pyruvate kinase. The compounds are short-chained pyruvates which have no utility as surfactant materials. Further, there is no teaching at all that these compounds can be used as intermediates to prepare a beneficial reagent or of their use in compositions.

Certain commercially available sulfosuccinic alkyl esters are similar to the compounds of the invention. For example, Caryl, C. R., Industrial and Eng. Chem., 33 (6): 731 (1941) teaches compounds in which an alkyl ester of succinic acid is attached to a sulfonate group. These compounds are both structurally and chemically distinct from the sulfooxyalkanoate esters of the invention in that they comprise a sulfonate group rather than a sulfate group. The sulfate group is much more difficult to hydrolyze and will not accordingly readily provide a beneficial reagent such as is hypothesized is occurring with the compounds of the invention.

Stirton et al., Journal Amer. Oil Chem. Soc., 39: 490 (1962) teaches alkyl sulfoalkanoate compounds. Smith et al., Journal Amer Oil Chem. Soc., 44:405 (1967) teaches $\alpha$-sulfo fatty acid ester compounds. Once again, both of these references teach sulfonate compounds rather than sulfate compounds. Sulfonate compounds are far less soluble and structurally unrelated to the sulfate compounds of the invention.

None of the compounds taught in the art are sulfate surfactant compounds which are readily able to hydrolyze and from a beneficial reagent in the skin.

Thus, it would be useful to provide compositions comprising novel molecules (other than the phosphate esters mentioned above) which contain a salt (i.e., at least a partial salt of one portion and an ester group in the other portion) such that (1) a hydroxy carboxylic acid ester; (2) a hydroxy carboxylic acid; (3) a sulfooxy carboxylate; and/or (4) an alcohol (e.g., fatty acid alcohol or glycerol) may form when the molecule in the composition is metabolized by enzymes in the skin or is hydrolyzed upon contact with the skin.

It is a further objective of the invention to provide compositions containing surfactants (having the beneficial reagent) which, as surfactants, are also relatively calcium insensitive, may foam well and are mild to the skin.

SUMMARY OF THE INVENTION

The present invention relates to personal product compositions and to novel alkyl sulfooxy alkanoate compounds therein. These surfactants are useful in that they are mild, they may foam well, they are calcium insensitive, and they provide a beneficial reagent component to the skin. The personal product compositions comprising these surfactants may be soap for compositions, body or facial cleaning compositions or toothpaste compositions, among others.

The sulfooxy alkanoate used in the compositions is a salt (or partial salt) in which hydrogen, an alkali metal an alkaline earth metal, ammonium, alkyl ammonium, alkanolamine, cationic amino acids (e.g., arginine), or other salt forming cation is attached to one of the single bonded sulfur oxygens and in which an alkyl group is attached to the other single bonded sulfur oxygens, wherein the alkyl group contains an ester group. While not wishing to be bound by theory, it is hypothesized that the ester-containing group attached to the sulfoxy oxygen is capable of forming (1) a hydroxy carboxylic acid ester (if cleaved only at the left of the oxygen bonded to the sulfur atom); (2) a hydroxy carboxylic acid (if cleaved at the left of the oxygen bonded to the sulfur and between the carboxylate oxygen and the alkyl group attached to the carboxylate oxygen; (3) a sulfooxy carboxylate (if cleaved only between the carboxylate oxygen and the alkyl group attached to the carboxylate oxygen; and/or (4) a free alcohol such as fatty alcohol or glycerol (as a by-product of the cleavage of the carboxylate oxygen and the alkyl group) when the sulfooxy ester surfactant molecule is metabolized or hydrolyzed.

Preferably, the final product after metabolism or hydrolysis is the hydroxy acid ester.

More particularly, the sulfate ester molecule is defined by formula I below:

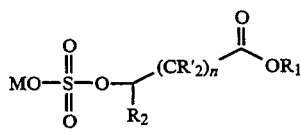

wherein:

M is an alkali metal such as lithium, sodium or potassium, an alkaline earth metal such as calcium, magnesium or strontium, ammonium, alkyl ammonium wherein the alkyl group is preferably a straight chain group having 1 to 22 carbons, alkanolamine, a cationic amino acid such as arginine or other salt forming cation such as, for example, a substituted pyridinium;

R' is hydrogen;

$R_2$ is hydrogen, a straight chain alkyl group having 1 to 6 carbons wherein the carbons should not be substituted with an esterifiable group such as a hydroxy group; a branched chain alkyl having 4 to 30 carbons (the carbons should again not be substituted with an esterifiable group such as a hydroxy group); a straight or branched chain alkyl aryl group (preferably alkyl phenyl) wherein the alkyl group may comprise 1-18 carbon atoms and wherein said alkyl aryl group may be condensed with a 2-5 carbon alkylene oxide; an aliphatic group having 6 to 30 carbons condensed with a 2-5 carbon alkylene oxide (encompassing the group of condensed alkyl aryl groups); a straight or branched-chain fluoroalkyl group having 5 to 23 carbons; wherein any of the alkyl groups described above may be linked by an ester group, amide, quaternary ammonium or heteroatom such as sulfur, oxygen or nitrogen;

$R_1$ is a straight chain alkyl group having at least 8 carbon atoms; and n=0 to 2.

The invention is further concerned with methods for producing the above-identified molecule used in the compositions of the invention.

DETAILED DESCRIPTION OF THE INVENTION

The present invention provides personal product compositions comprising novel sulfooxy alkanoate surfactants which are designed to deliver certain benefit enhancing agents (e.g., moisturizers) to the skin. Since it is known that hydroxy acids, e.g., hydroxy caprylic acid (HCA), lactic acid and analogs thereof provide a softening or plasticizing effect on skin, (see also U.S. Pat. No. 4,197,316; and Hall et al. *J. Soc. Cosmet Chem.*, 37: 397–407 (1986)) the surfactant molecules used in the compositions of the invention have been designed to incorporate a component which may, upon being metabolized or hydrolyzed, form a hydroxy carboxylic acid ester, a hydroxy carboxylic acid, a sulfooxy carboxylate and/or a free alcohol such as a fatty acid alcohol or glycerol. Preferably, the surfactant will metabolize or hydrolyze to form the hydroxy carboxylic acid or alcohol.

Compositions

The personal product compositions of the invention may be, for example, soap bar compositions, facial or body cleansing compositions, shampoos for hair or body, conditioners, cosmetic compositions or dental compositions.

In one embodiment of the invention, the surfactant of the invention may be used, for example, in a toilet bar formulation.

Typical soap bar compositions are those comprising fatty acid soaps used in composition with a detergent other than fatty acid soap and free fatty acids. Mildness improving salts, such as alkali metal salt or isethionate, are also typically added. In addition other ingredients, such as germicides, perfumes, colorants, pigments, suds-boosting salts and anti-mushing agents may also be added.

Fatty acid soaps are typically alkali metal or alkanol ammonium salts of aliphatic alkane or alkene monocarboxylic acids. Sodium, potassium, mono-, di and triethanol ammonium cations, or combinations thereof, are suitable for purposes of the invention. The soaps are well known alkali metal salts of natural or synthetic aliphatic (alkanoic or alkenoic) acids having about 8 to 22 carbons, preferably 12 to about 18 carbons. They may be described as alkali metal carboxylates of acrylic hydrocarbons having about 12 to 22 carbons.

Examples of soap which may be used may be found in U.S. Pat. No. 4,695,395 to Caswell et al. and U.S. Pat. No. 4,260,507 (Barrett), both of which are incorporated herein by reference.

Fatty acid soaps will generally comprise greater than 25% of the composition, generally from 30–98%. Preferably, the amount of soap will range from 40% to 70% by weight of the composition.

The compositions will also generally comprise a non-soap detergent which is generally chosen from anionic, nonionic, cationic, zwitterionic or amphoteric synthetic detergent materials or mixtures thereof. These surfactants are well known in the art and are described, for example, in U.S. Pat. Nos. 4,695,395 and 4,260,507 discussed above. These non-soap actives may comprise from 0 to 50% of the composition.

A certain amount of free fatty acids of 8 to 22 carbons are also desirably incorporated into soap compositions to act as superfatting agents or as skin feel and creaminess enhancers. If present, the free fatty acids comprise between 1 and 15% of the compositions.

A preferred mildness improving salt which may be added to soap compositions is a simple unsubstituted sodium isethionate. This may be present as 0.1 to 50% of the composition, preferably 0.5% to 25%, more preferably 2% to about 15% by weight. Other mildness co-actives which may be used include betain compounds or ether sulphates. These also may be present at 0.1 to 50% of the composition, preferably 0.5% to 25%.

The sulfate ester surfactant of the invention may comprise 0.01 to 45% by weight of the composition (as the monoester), preferably 25% to 40%, and 0.01% to 10% of the composition (as the diester), preferably 0.01% to 5%.

Other optional ingredients which may be present in soap bar compositions are moisturizers such as glycerin, propylene glycol, sorbitol, polyethylene glycol, ethoxylated or methoxylated ether of methyl glucose etc.; water-soluble polymers such as collagens, modified cellulases (such as Polymer JR ®), guar gums and polyacrylates; sequestering agents such as citrate, and emollinets such as silicones or mineral oil. Another useful set of ingredients are various cosurfactants and non-soap detergents.

In a second embodiment of the invention the surfactant of the invention may be present in a facial or body cleansing composition. Examples of such cleaning compositions are described, for example, in U.S. Pat. No. 4,812,253 to Small et al. and U.S. Pat. No. 4,526,710 to Fujisawa, both of which are hereby incorporated by reference.

Typically, cleansing compositions will comprise a fatty acid soap together with a non-soap surfactant, preferably a mild synthetic surfactant. Cleaning compositions will also generally include a moisturizer or emollient and polymeric skin feel and mildness aids. The compositions may further optionally include thickener, conditioners, water soluble polymers, dyes, hydrotropes brighteners, perfumes and germicides.

the fatty acid soaps used are such as those described above in uses in detergent bar formulations. These soaps are typically alkali metal or alkanol ammonium salts of aliphatic or alkene monocarboxylic salts. Sodium, potassium, mono-, di- and triethanol ammonium cations, or combinations thereof are suitable. Preferred soaps are 8 to 24 carbon half acid salts of, for example, triethanolamine.

Surfactants can be chosen from anionic, nonionic, cationic, zwitterionic or amphoteric materials or mixtures thereof such as are described in U.S. Pat. No. 4,695,395 mentioned above, or in U.S. Pat. No. 4,854,333 to Inman et al, hereby incorporated by reference.

Moisturizers are included to provide skin conditioning benefits and improve mildness. This term is often used as synonymous with emollient and is then used to describe a material which imparts a smooth and soft feeling to skin surface.

There are two ways of reducing water loss from the stratum corneum. One is to deposit on the surface of the skin an occlusive layer which reduces the rate of evaporation. The second method is to add nonocclusive hydroscopic substances to the stratum corneum which will retain water, and make this water available to the stratum corneum to alter its physical properties and produce a cosmetically desirable effect. Nonocclusive moisturizers also function by improving the lubricity of the skin.

Both occlusive and nonocclusive moisturizers can work in the present invention. Some examples of moisturizers are long chain fatty acids, liquid water-soluble polyols, glycerin, propylene glycol, sorbitol, polyethylene glycol, ethoxylated/propoxylated ethers of methyl glucose (e.g., methyl gluceth-20) and ethoxylated/propoxylated ethers of lanolin alcohol (e.g., Solulan-75).

Preferred moisturizers are coco and tallow fatty acids. Some other preferred moisturizers are the nonocclusive liquid water soluble polyols and the essential amino acid compounds found naturally in the skin.

Other preferred nonocclusive moisturizers are compounds found to be naturally occurring in the stratum corneum of the skin, such as sodium pyrrolidone carboxylic acid, lactic acid, urea, L-proline, guanidine and pyrrolidone. Examples of other nonocclusive moisturizers include hexadecyl, myristyl, isodecyl or isopropyl esters of adipic, lactic, oleic, stearic, isostearic, myristic or linoleic acids, as well as many of their corresponding alcohol esters (sodium isostearoyl-2 lactylate, sodium capryl lactylate), hydrolyzed protein and other collagen-derived proteins, aloe vera gel and acetamide MEA.

Some occlusive moisturizers include petrolatum, mineral oil, beeswax, silicones, lanolin and oil-soluble lanolin derivatives, saturated and unsaturated fatty alcohols such as behenyl alcohol, squalene and squalene, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil.

Other examples of both types of moisturizers are disclosed in "Emollients—A Critical Evaluation," by J. Mausner, Cosmetics & Toiletries, May 1981, incorporated herein by reference.

The polymeric skin feel and mildness aids useful in the present invention are the cationic, anionic, amphoteric, and the nonionic polymers used in the cosmetic field. Reduced skin irritation benefits as measured by patch testing of cationic and nonionic types of polymers are set out in "Polymer JR for Skin Care" Bulletin, by Union Carbide, 1977. The cationics are preferred over the others because they provide better skin feel benefits.

The amount of polymeric skin feel and mildness aids found useful in the composition of the present invention is from about 0.01% to about 5%, preferably from about 0.3% to about 4%. In bar compositions with less than 5.5% soap, the polymer is used at a level of 2% to 5%, preferably 3% or more.

Other types of high molecular weight polymeric skin feel and skin mildness aids, such as nonionic guar gums, Merquats 100 and 550, made by Merck & Co, Inc.; JAGUAR C-14-S made by Stein Hall; Mirapol A15 made by Miranol Chemical Company, Inc.; and Galactasol 811, made by Henkel, Inc.; plus others, are usable. The polymer also provides enhanced creamy lather benefits.

The nonionic polymers found to be useful include the nonionic polysaccharides, e.g., nonionic hydroxypropyl guar gums, offered by Celanese Corp. A preferred nonionic hydroxypropyl guar gum material is JAGUAR ® HP-60 having molar substitution of about 0.6. About class of useful nonionics is the cellulosic nonionic polymers, e.g., HEC and CMC.

The cationic polymers employed in this invention also provide a desirable silky, soft, smooth in-use feeling. The preferred level for this invention is 0.1–5% of the composition. There is a reason to believe that the positively charged cationic polymers can bind with negatively charges sites on the skin to provide a soft skin feel after use. Not to be bound by any theory, it is believed that the greater the charge density of the cationic polymer, the more effective it is for skin feel benefits.

Other suitable cationic polymers are copolymers of dimethylaminoethylmethacrylate and acrylamide and copolymers of dimethyldiallylammonium chloride and acrylamide in which the ratio of the cationic to neutral monomer units has been selected to give a copolymer having a cationic charge. Yet other suitable types of cationic polymers are the cationic starches, e.g., Sta-Lok ®300 and 400 made by Staley, Inc.

A more complete list of cationic polymers useful in the present invention is described in U.S. Pat. No. 4,438,095, to Grolier/Allec, issued Mar. 20, 1984, incorporated herein by reference. Some of the more preferred cationics are listed in Col. 3, Section 2; Col. 5, section 8; Col. 8, section 10; and Col. 9, lines 10–15 of the Grollier/Allec patent, incorporated herein by reference.

In a third embodiment of the of the invention, the surfactant of the invention may be used, for example, in a bar or body shampoo. Examples of such compositions are described in U.S. Pat. No. 4,854,333, to Inman and U.S. Pat. No. 4,526,710 to Fujisawa, both of which are hereby incorporated by reference.

The shampoo compositions which may be used typically comprises a surfactant selected from any one of a wide variety of surfactants known in the art (such as those described in U.S. Pat. No. 4,854,333, incorporated herein by reference). The shampoo compositions may additionally comprise a compound considered useful for treating dandruff, e.g. selenium sulfide.

The compositions all may also optionally comprise a suspending agent, for example, any of several acryl derivative materials or mixtures thereof. Among these are ethylene glycol esters of fatty acids having 16 to 22 carbons. Preferred suspending agents include ethylene glycol stearates, both mono- and distearate. Preferred alkanol amides are stearic monoethanolamide, stearic diethanolamide and stearic monoisopropanolamide. Still other long chain acyl derivatives include long chain esters of long chain fatty acids (e.g., stearyl stearate, cetyl palmitate), glyceryl esters (e.g. glyceryl distearate), and long chain esters of long chain alkanol amides (e.g., stearamide DEA distearate, stearamide MEA stearate).

Still other suitable suspending agents are alkyl (16 to 22 carbon) dimethyl amine oxides, such as stearyl dimethyl amine oxide. If the compositions contain an amine oxide or a long chain acyl derivative as a surfactant, these components may also provide the suspending function and additional suspending agent may not be needed.

Xanthan gum is another aspect used to suspend, for example, selenium sulfide which may be in the present compositions. This biosynthetic gum material is commercially available and is a heteropolysaccharide with a molecular weight of greater than 1 million. It is believed to contain D-glucose, D-mannose and D-glucoronate in the molar ratio of 2.8:2.0:2.0. The polysaccharide is partially acetylated with 4.7% acetyl. Supplemental information on these agents is found in Whistler, Roy L. (Editor), *Industrial Gums—Polysaccharides and Their Derivatives* New York: Academic Press, 1973. Kelso, a Division of Merck & Co., Inc., offers xanthan gum as KeltrolR.

A particularly preferred suspending system comprises a mixture of xanthan gum, present at a level of from about 0.05% to about 1.0%, preferably from about 0.2% to about 0.4%, of the compositions, together with magnesium aluminum silicate ($Al_2Mg_8Si_2$), present at a level of from 0.1% to about 3.0%, preferably from about 0.5% to about 2.0%, of the compositions. Magnesium aluminum silicate occurs naturally in such smectite minerals as colerainite, saponite and sapphire. Refined magnesium aluminum silicates useful herein are readily available, for example as veegum, manufactured by R. T. Vanderbilt Company, Inc. Mixtures of suspending agents are also suitable for use in the compositions of this invention.

Other useful thickening agents are the cross-linked polyacrylates such as those manufactured by B. F. Goodrich and sold under the Carbopol ® tradename.

Another optional component for use in the present compositions is an amide. The amide used in the present compositions can be any of the alkanolamides of fatty acids known for use in shampoos. These are generally mono- and diethanolamides of fatty acids having from about 8 to 24 carbon atoms. Preferred are coconut monoethanolamide, lauric diethanolamide and mixtures thereof. The amide is present at a level of from about 1% to about 10% of the compositions.

The compositions may also contain nonionic polymer material which is used at a low level to aid in dispersing particles. The material can be any of a large variety of types including cellulosic materials such as hydroxypropyl methyl cellulose, carboxymethyl cellulose, hydroxyethyl cellulose and sodium carboxymethyl cellulose as well as mixtures of these materials. Other materials include alginates, polyacrylic acids, polyethylene glycol and starches, among many others. The nonionic polymers are discussed in detail in *Industrial Gums*, edited by Roy L. Whistler, Academic Press, Inc., 1973, and *Handbook of Water-Soluble Gums and Resins*, edited by Robert L. Davidson, McGraw-Hill Inc., 1980. Both of these books in their entirety are incorporated herein by reference.

When included, the nonionic polymer is used at a level of from about 0.001% to about 0.1%, preferably from about 0.002% to about 0.05%, of the composition. Hydroxypropyl methyl cellulose is the preferred polymer.

Another suitable optional component useful in the present compositions is a nonvolatile silicone fluid.

The nonvolatile silicone fluid may be either a polyalkyl siloxane, a polyaryl siloxane, a polyalkylaryl siloxane or a polyether siloxane copolymer and is present at a level of from about 0.1% to about 10.0%, preferably from about 0.5% to about 5.0%. Mixtures of these fluids may also be used and are preferred in certain executions. The dispersed silicone particles should also be insoluble in the shampoo matrix. This is the meaning of "insoluble" as used herein.

The essentially nonvolatile polyalkyl siloxane fluids that may be used include, for example, polydimethyl siloxanes with viscosities ranging from about 5 to about 600,000 centistokes at 25° C. These siloxanes are available, for example, from the General Electric Company as the Viscasil series and from Dow Corning as the Dow Corning 200 series. The siloxane viscosity can be measured by means of a glass capillary viscometer as set forth in Dow Corning Corporate Test Method CTM0004, Jul. 20, 1970. Preferably the viscosity of these siloxanes range from about 350 centistokes to about 100,000 centistokes.

The essentially nonvolatile polyether siloxane copolymer that may be used is, for example, a polypropylene oxide modified dimethylpolysiloxane (e.g., Dow Corning DC-1248), although ethylene oxide or mixtures of ethylene oxide and propylene oxide may also be used.

Suitable silicone fluids are described in U.S. Pat. No. 2,826,551, Geen; U.S. Pat. No. 3,946,500, Jun. 22, 1976, Drakoff; U.S. Pat. No. 4,364,837, Pader; and British Patent 849,433, Woolston. All of these patents are incorporated herein by reference. Also incorporated herein by reference is Silicon Compounds, distributed by Petrarch Systems, Inc., 1984. This reference provides a very good listing of suitable silicone materials.

Another silicone material useful is silicone gum. Silicone gums are described by Petrarch and others including U.S. Pat. No. 4,152,416, May 1, 1979, Spitzer, et al., and Noll, *Chemistry and Technology of Silicones*, New York, Academic Press, 1968. Useful silicone gums are also described in General Electric Silicone Rubber Product Data Sheets SE 30, SE 33, SE 54 and SE 76. All of these references are incorporated herein by reference. "Silicone gum" materials denote high molecular weight polydiorganosiloxanes having a mass molecular weight of from about 200,000 to about 1,000,000. Specific examples include polydimethylsiloxane, (polydimethylsiloxane) (methylvinylsiloxane) copolymer, poly(dimethylsiloxane) (diphenyl) (methylvinylsiloxane) copolymer, and mixtures thereof. Mixtures of silicone fluids and silicone gums are also useful herein.

The shampoos herein can contain a variety of other nonessential optional components suitable for rendering such compositions more formulatable, or aesthetically and/or cosmetically acceptable. Such conventional optional ingredients are well-known to those skilled in the art and include, e.g., preservatives, such as benzyl alcohol, methyl paraben, propyl paraben, and imidazolinidyl urea; cationic surfactants, such as cetyl trimethyl ammonium chloride, lauryl trimethyl ammonium chloride, tricetyl methyl ammonium chloride, stearyldimethyl benzyl ammonium chloride, and di(partially hydrogenated tallow) dimethylammonium chloride; menthol; thickeners and viscosity modifiers, such as block polymers of ethylene oxide and propylene oxide such as Pluronic F88 offered by BASA Wyandotte, sodium chloride, sodium sulfate, propylene glycol, and ethyl alcohol; pH adjusting agents, such as citric acid, succinic acid, phosphoric acid, sodium hydroxide, sodium carbonate; perfumes; dyes; and sequestering agents, such as disodium ethylenediamine tetraacetate. Such agents generally are used individually at a level of from about 0.01% to about 10%, preferably from about 0.5% to about 5.0%, of the composition.

In a fourth embodiment of the invention, the surfactant of the invention may be used in a conditioner composition such as is taught and described in U.S. Pat. No. 4,913,828 to Caswell et al. which is hereby incorporated by reference.

More particularly, conditioner compositions are those containing a conditioning agent (e.g. alkylamine compounds) such as those described in U.S. Pat. No. 4,913,828.

In a fifth embodiment of the invention, the surfactant may be used in a cosmetic composition, such as is taught and is describe in EP 0,371,803.

Such compositions generally comprise thickening agents, preservatives and further additions.

The composition may comprise polymer thickener in an amount sufficient to adjust the viscosity of the composition, so as to facilitate dispensing it conveniently onto the body surface.

Examples of polymer thickeners include: anionic cellulose materials, such as sodium carboxy methyl cellulose; anionic polymer such as carboxy vinyl polymers, for example, Carbomer 940 and 941; nonionic cellulose materials, such as methyl cellulose and hydroxy propyl methyl cellulose; cationic cellulose materials, such as Polymer JR 400; cationic gum materials, such as Jaguar C13 S; other gum materials such as gum acacia, gum tragacanth, locust bean gum, guar gum and carrageenan; proteins, such as albumin and protein hydrolysates; and clay materials, such as bentonite, hectorite, magnesium aluminum silicate, or sodium magnesium silicate.

Generally, the thickening agent may comprise from 0.05 to 5%, preferably 0.1 to 1% by weight of the composition.

The composition according to the invention can also optionally comprise a preservative to prevent microbial spoilage.

Examples of preservatives include:

(i) Chemical preservatives, such as ethanol, benzoic acid, sodium benzoate, sorbic acid, potassium sorbate, sodium propionate and the methyl, ethyl, propyl and butyl esters of p-hydroxybenzoic acid 2-bromo-2-nitropropane-1, 3-diol, phenoxyethanol, dibromodicyanobutane, formalin and Tricolsan. The amount of chemical preservative optionally to be incorporated in the composition according to the invention will generally be from 0.05 to 5%, preferably from 0.01 to 2% by weight, the amount chosen being sufficient to arrest microbial proliferation.

(ii) Water activity depressants, such as glycerol, propylene glycol, sorbitol, sugars and salts, for examples alkali metal halides, sulphates and carboxylates. When employing a water activity depressant, sufficient should be incorporated in the composition according to the invention to reduce the water activity ($a_\omega$) from 1 to <0.9, preferably to <0.85 and most preferably <0.8, the lowest of these values being that at which yeasts, molds and fungi will not proliferate.

The composition can also contain other optional adjuncts, which are conventionally employed in compositions for topical application to human skin. These adjuncts, when present, will normally form the balance of the composition.

Examples of optional adjuncts include vehicles, the selection of which will depend on the required product form of the composition. Typically, the vehicle when present, will be chosen from diluents, dispersants or carriers for the dialkyl or dialkenyl phosphate salt so as to ensure an even distribution of it when applied to the skin.

Compositions according to this invention can include water as a vehicle, usually when at least one other cosmetically-acceptable vehicle.

Vehicles other than water can be used in compositions according to the invention can include liquids or solids as emollients, solvents, humectants, thickeners and powders. Examples of each of these types of vehicles, which can be used singly or as mixtures of one or more vehicles, are as follows:

Emollients, such as stearyl alcohol, glyceryl monolaurate, glyceryl monoricinoleate, glyceryl monostearate, propane-1, 2-diol, butane-1.3 diol, docosan-1,2-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, soybean oil, sunflower seed oil, olive oil, sesame seed oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluoromethane, monochlorodifluoromethane, trichlorotrifluoromethane, propane, butane, isobutane, dimethyl ether, carbon dioxide, nitrous oxide;

Solvents, such as ethyl alcohol, methylene chloride, isopropanol, acetone, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate.

The cosmetically acceptable vehicle, when present, will usually form from 0.01 to 99.9%, preferably from 59 to 98% by weight of the composition, and can, in the absence of other cosmetic adjuncts, form the balance of the composition.

A wide variety of conventional sunscreening agents, such as those described in U.S. Pat. No. 4,919,934 to Deckner et al. hereby incorporated by reference, may also be used in the cosmetic compositions of the invention.

Such agents include, for example, p-Aminobenzoic acid, its salts and its derivatives, anthranilates, salicylates, cinnamic acid derivatives, di- and trihydroxy cinnamic acid derivatives, hydrocarbons such as diphenylbutadiene and stilbene, dibenzalacetone and benzalacetophenone, naphthasulfonates, di-hydroxy naphtholic acid and its salts, hydroxy diphenysulfonate, coumarin derivatives, diazoles, quinine salts, quinoline derivatives, hydroxy or methoxy substituted benzophenones, uric or vilouric acid, tannic acid and its derivatives, hydroquinone, and benzophenones.

In a sixth embodiment of the invention, the surfactant may be used in a toothpaste composition such as is taught and is described in U.S. Pat. No. 4,935,227 to Duckworth, which is hereby incorporated by reference.

Such compositions generally comprise abrasive gels (e.g. calcium carbonate), oral therapeutic agents (e.g., fluorine containing compound), coactives, flavoring agents, sweetening agents, humectants and binding or thickening gels.

Preferred toothpastes of this invention comprise 0 to 1.5% by weight of anionic surfactant. In more preferred products the amount of anionic surfactant is 0 to 1% by weight with most preferred amounts being 0 to 0.75% by weight.

Toothpastes of this invention may include other surfactants, especially non-ionic surfactants.

Toothpaste of the invention will also comprise the usual additional ingredients in particular humectant binder or thickening agent.

Humectants which may be used include glycerol, sorbitol syrup, polyethylene glycol, lactitol, xylitol or hydrogenated corn syrup. The total amount of humectant present will generally range from 10% to 85% by weight of the toothpaste.

Numerous binding or thickening agents have been indicated for use in toothpastes, preferred ones being sodium carboxymethylcellulose, cross-linked polyacrylates and xanthan gum. Other include natural gum binders such as gum tragacanth, gum karaya and gum arabic, Irish moss, alginates, and carrageenans. Silica thickening agents include the silica aerogels and various precipitated silicas. Mixtures of binders and thickeners may be used. The amount of binder and thickening agent included in a toothpaste is generally between 0.1 and 15% by weight.

In a seventh embodiment of the invention, the molecule of the invention may be used in a light duty liquid detergent composition such as those taught in U.S. Pat. No. 4,671,894 to Lamb et al, hereby incorporated by reference, which patent is also hereby incorporated by reference.

Generally such compositions comprise a mixture of sulphate and sulphonate anionic surfactants together with a suds stabilizing agent. These compositions may also comprise nonionic surfactants designed to reduce the level of non-performing ingredients such as solvents and hydrotropes and zwitterionic surfactants for providing enhanced grease and particulate soil removal performance.

Among other ingredients which may also be used in such compositions are opacifiers (e.g. ethylene glycol distearate), thickeners (e.g., guar gum), antibacterial agents, antitarnish agents, heavy metal chelators (e.g. (ETDA), perfumes and dyes.

In an eighth embodiment of the invention the molecule of the invention may be used in underarm deodorant/antiperspirant compositions such as those taught in U.S. Pat. No. 4,919,934 to Deckner, U.S. Pat. No. 4,944,937 to McCall and U.S. Pat. No. 4,944,938 to Patini, all of which patents are hereby incorporated by reference.

Such compositions generally comprise a cosmetic stick (gel or wax) composition which in turn generally comprises one or more liquid base materials (e.g., water, fatty acid and fatty alcohol esters, water-insoluble ethers and alcohols, polyorganosiloxanes); a solidifying agent for solidifying the liquid base; and an active component such as bacteriostats or fungistats (for antideodorant activity) or astringent metallic salts (for antiperspirant activity).

These compositions may also comprise hardeners, strenghteners, emollients, colorants, perfumes, and emulsifiers and fillers.

While various compositions are described above, these should not be understood to be limiting as to what other personal product compositions may be used since other compositions which may be known to those of ordinary skill in the art are also contemplated by this invention.

The Surfactant Molecule

More particularly, the molecule is defined by the formula:

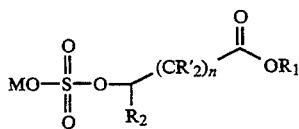

wherein:

M is an alkali metal such as lithium, sodium or potassium, an alkaline earth metal such as calcium, magnesium or strontium, ammonium, alkyl ammonium wherein the alkyl group is preferably a straight chain alkyl having 1 to 22 carbons, alkanolamine, a cationic amino acid such as arginine or other salt forming cation such as, for example, a substituted pyridinium;

R' is hydrogen;

$R_2$ is hydrogen, a straight chain alkyl group having 1 to 6 carbons wherein the carbons should not be substituted with an esterifiable group such as a hydroxy group; a branched chain alkyl having 4 to 30 carbons (again none of the carbons should be substituted with an esterifiable group such as a hydroxyl group); a straight or branched chain alkyl aryl group (preferably alkyl phenyl) wherein the alkyl group may comprise 1-18 carbon atoms and wherein said alkyl aryl group may be condensed with a 2-5 carbon alkylene oxide; an aliphatic group having 6 to 30 carbons condensed with a 2-5 carbon alkylene oxide (encompassing the group of condensed alkyl aryl groups); a straight or branched-chain fluoroalkyl group having 5 to 23 carbons; wherein any of the alkyl groups described above may be linked by an ester group, amide, quaternary ammonium or heteroatom such as sulfur, oxygen or nitrogen;

$R_1$ is a straight chain alkyl group having at least 8 carbons; and n=0 to 2.

The section of the molecule attached to the singly bonded sulfoxy oxygen (but not M) is what is considered the hydroxy acid (if cleaved between the carboxylate oxygen and the alkyl group) or hydroxy acid ester portion (if not cleaved) of the molecule.

The following compounds are illustrative surface active or self organizer molecules within the present invention. It is also to be understood that these molecules are salts or partly formed salts:

decyl 2-(hydrogen sulfooxy)acetate
dodecyl 2-(hydrogen sulfooxy)acetate
tetradecyl 2-(hydrogen sulfooxy)acetate
hexadecyl 2-(hydrogen sulfooxy)acetate
octadecyl 2-(hydrogen sulfooxy)acetate
docosyl 2-(hydrogen sulfooxy)acetate
butyl 2-(hydrogen sulfooxy)acetate
hexyl 2-(hydrogen sulfooxy)acetate
octyl 2-(hydrogen sulfooxy)acetate
nonyl 2-(hydrogen sulfooxy)acetate
tetracosyl 2-(hydrogen sulfooxy)acetate
2-ethylhexyl 2-(hydrogen sulfooxy)acetate
2-ethyldecyl 2-(hydrogen sulfooxy)acetate
2-ethyldodecyl 2-(hydrogen sulfooxy)acetate
2-propyldecyl 2-(hydrogen sulfooxy)acetate
2-butyldecyl 2-(hydrogen sulfooxy)acetate
2-octyldodecyl 2-(hydrogen sulfooxy)acetate
2-dodecyl hexadecyl 2-(hydrogen sulfooxy)acetate
2-tetradecyloctadecyl 2-(hydrogen sulfooxy)acetate
2-ethyldecyl 2-(hydrogen sulfooxy)acetate
hexenyl 2-(hydrogen sulfooxy)acetate
decenyl 2-(hydrogen sulfooxy)acetate
dodecenyl 2-(hydrogen sulfooxy)acetate
tetradecenyl 2-(hydrogen sulfooxy)acetate
hexadecenyl 2-(hydrogen sulfooxy)acetate
octadecenyl 2-(hydrogen sulfooxy)acetate
docosenyl 2-(hydrogen sulfooxy)acetate
tetracosenyl 2-(hydrogen sulfooxy)acetate
nonylphenyl 2-(hydrogen sulfooxy)acetate
decylphenyl 2-(hydrogen sulfooxy)acetate
dodecylphenyl 2-(hydrogen sulfooxy)acetate
tetradecylphenyl 2-(hydrogen sulfooxy)acetate
2-(2-ethoxyethoxy)ethyl 2-(hydrogen sulfooxy)acetate
2-(2-butoxyethoxy)ethyl 2-(hydrogen sulfooxy)acetate
fluorodecyl 2-(hydrogen sulfooxy)acetate
trifluorooctyl 2-(hydrogen sulfooxy)acetate
pentadecafluorodecyl 2-(hydrogen sulfooxy)acetate
fluorododecyl 2-(dihydrogen phosphoxy)acetate
2-(N,N-ditallow-N-methylammonium)ethyl 2-(hydrogen sulfooxy)acetate
3-(N,N-ditallow-N-methylammonium)propyl 2-(hydrogen sulfooxy)acetate
2-(N-nonyl-N,N-dimethylammonium)ethyl 2-(hydrogen sulfooxy)acetate
2-(N-sterayl-N,N-dimethylammonium)ethyl 2-(hydrogen sulfooxy)acetate
2-(N-dodecyl-N,N-dimethylammonium)ethyl 2-(hydrogen sulfooxy)acetate
pentyl 2-(hydrogen sulfooxy)propionate
hexyl 2-(hydrogen sulfooxy)propionate
octyl 2-(hydrogen sulfooxy)propionate
nonyl 2-(hydrogen sulfooxy)propionate
decyl 2-(hydrogen sulfooxy)propionate
dodecyl 2-(hydrogen sulfooxy)propionate
tetradecyl 2-(hydrogen sulfooxy)propionate
hexadecyl 2-(hydrogen sulfooxy)propionate
octadecyl 2-(hydrogen sulfooxy)propionate
docosyl 2-(hydrogen sulfooxy)propionate
tetracosyl 2-(hydrogen sulfooxy)propionate
2-ethylhexyl 2-(hydrogen sulfooxy)propionate
2-ethyldecyl 2-(hydrogen sulfooxy)propionate
2-ethyldodecyl 2-(hydrogen sulfooxy)propionate
2-propyldecyl 2-(hydrogen sulfooxy)propionate
2-butyldoecyl 2-(hydrogen sulfooxy)propionate
2-octyldodecyl 2-(hydrogen sulfooxy)propionate
2-dodecyl hexadecyl 2-(hydrogen sulfooxy)propionate
2-tetradecyloctadecyl 2-(hydrogen sulfooxy)propionate
2-ethyldecyl 2-(hydrogen sulfooxy)propionate
hexenyl 2-(hydrogen sulfooxy)propionate
decenyl 2-(hydrogen sulfooxy)propionate
dodecenyl 2-(hydrogen sulfooxy)propionate tetradecenyl 2-(hydrogen sulfooxy)propionate
hexadecenyl 2-(hydrogen sulfooxy)propionate
octadecenyl 2-(hydrogen sulfooxy)propionate
docosenyl 2-(hydrogen sulfooxy)propionate
tetracosenyl 2-(hydrogen sulfooxy)propionate
nonylphenyl 2-(hydrogen sulfooxy)propionate
decylphenyl 2-(hydrogen sulfooxy)propionate
dodecylphenyl 2-(hydrogen sulfooxy)propionate
tetradecylphenyl 2-(hydrogen sulfooxy)propionate
2-(2-ethoxyethoxy)ethyl 2-(hydrogen sulfooxy)propionate
2-(2-butoxyethoxy)ethyl 2-(hydrogen sulfooxy)propionate
fluorodecyl 2-(hydrogen sulfooxy)propionate
trifluorooctyl 2-(hydrogen sulfooxy)propionate
pentadecafluorodecyl 2-(hydrogen sulfooxy)propionate
fluorododecyl 2-(hydrogen sulfooxy)propionate
2-(N,N-ditallow-N-methylammonium)ethyl 2-(hydrogen sulfooxy)propionate
3-(N,N-ditallow-N-methylammonium)propyl 2-(hydrogen sulfooxy)propionate
2-(N-nonyl-N,N-dimethylammonium)ethyl 2-hydrogen sulfooxy)propionate
2-(N-sterayl-N,N-dimethylammonium)ethyl 2-(hydrogen sulfooxy)propionate
2-(N-dodecyl-N,N-dimethylammonium)ethyl 2-(hydrogen sulfooxy)propionate
hexyl 3-(hydrogen sulfooxy)propionate
octyl 3-(hydrogen sulfooxy)propionate
nonyl 3-(hydrogen sulfooxy)propionate
decyl 3-(hydrogen sulfooxy)propionate
dodecyl 3-(hydrogen sulfooxy)propionate
tetradecyl 3-(hydrogen sulfooxy)propionate
hexadecyl 3-(hydrogen sulfooxy)propionate
octadecyl 3-(hydrogen sulfooxy)propionate
docosyl 3-(dihydrogen sulfooxy)propionate
tetracosyl 3-(hydrogen sulfooxy)propionate
2-ethylhexyl 3-(hydrogen sulfooxy)propionate
2-ethyldecyl 3-(hydrogen sulfooxy)propionate
2-ethyldodecyl 3-(hydrogen sulfooxy)propionate
2-propyldecyl 3-(hydrogen sulfooxy)propionate
2-butyldoecyl 3-(hydrogen sulfooxy)propionate
2-octyldodecyl 3-(hydrogen sulfooxy)propionate
2-dodecyl hexadecyl 3-(hydrogen sulfooxy)propionate
2-tetradecyloctadecyl 3-(hydrogen sulfooxy)propionate
2-ethyldecyl 3-(hydrogen sulfooxy)propionate
hexenyl 3-(hydrogen sulfooxy)propionate
decenyl 3-(hydrogen sulfooxy)propionate
dodecenyl 3-(hydrogen sulfooxy)propionate
tetradecenyl 3-(hydrogen sulfooxy)propionate
hexadecenyl 3-(hydrogen sulfooxy)propionate
octadecenyl 3-(hydrogen sulfooxy)propionate
docosenyl 3-(hydrogen sulfooxy)propionate
tetracosenyl 3-(hydrogen sulfooxy)propionate
nonylphenyl 3-(hydrogen sulfooxy)propionate
decylphenyl 3-(hydrogen sulfooxy)propionate
dodecylphenyl 3-(hydrogen sulfooxy)propionate
tetradecylphenyl 3-(hydrogen sulfooxy)propionate
2-(2-ethoxyethoxy)ethyl 3-(hydrogen sulfooxy)propionate
2-(2-butoxyethoxy)ethyl 3-(hydrogen sulfooxy)propionate
fluorodecyl 3-(hydrogen sulfooxy)propionate
trifluorooctyl 3-(hydrogen sulfooxy)propionate
pentadecafluorodecyl 3-(hydrogen sulfooxy)propionate
fluorododecyl 3-(hydrogen sulfooxy)propionate
2-(N,N-ditallow-N-methylammonium)ethyl 3-(hydrogen sulfooxy)propionate
3-(N,N-ditallow-N-methylammonium)propyl 3-(hydrogen sulfooxy)propionate
2-(N-nonyl-N,N-dimethylammonium)ethyl 3-(hydrogen sulfooxy)propionate
2-(N-sterayl-N,N-dimethylammonium)ethyl 3-(hydrogen sulfooxy)propionate
2-(N-dodecyl-N,N-dimethylammonium)ethyl 3-(hydrogen sulfooxy)propionate
hexyl 3-(hydrogen sulfooxy)butyrate
octyl 3-(hydrogen sulfooxy)butyrate
nonyl 3-(hydrogen sulfooxy)butyrate
decyl 3-(hydrogen sulfooxy)butyrate
dodecyl 3-(hydrogen sulfooxy)butyrate
tetradecyl 3-(hydrogen sulfooxy)butyrate
hexadecyl 3-(hydrogen sulfooxy)butyrate
octadecyl 3-(hydrogen sulfooxy)butyrate
docosyl 3-(hydrogen sulfooxy)butyrate
tetracosyl 3-(hydrogen sulfooxy)butyrate
2-ethylhexyl 3-(hydrogen sulfooxy)butyrate
2-ethyldecyl 3-(hydrogen sulfooxy)butyrate
2-ethyldodecyl 3-(hydrogen sulfooxy)butyrate
2-propyldecyl 3-(hydrogen sulfooxy)butyrate
2-butyldoecyl 3-(hydrogen sulfooxy)butyrate
2-octyldodecyl 3-(hydrogen sulfooxy)butyrate
2-dodecyl hexadecyl 3-(hydrogen sulfooxy)butyrate
2-tetradecyloctadecyl 3-(hydrogen sulfooxy)butyrate
2-ethyldecyl 3-(hydrogen sulfooxy)butyrate
hexenyl 3-(hydrogen sulfooxy)butyrate
decenyl 3-(hydrogen sulfooxy)butyrate
dodecenyl 3-(hydrogen sulfooxy)butyrate
tetradecenyl 3-(hydrogen sulfooxy)butyrate
hexadecenyl 3-(hydrogen sulfooxy)butyrate
octadecenyl 3-(hydrogen sulfooxy)butyrate
docosenyl 3-(hydrogen sulfooxy)butyrate
tetracosenyl 3-(hydrogen sulfooxy)butyrate
nonylphenyl 3-(hydrogen sulfooxy)butyrate
decylphenyl 3-(hydrogen sulfooxy)butyrate
dodecylphenyl 3-(hydrogen sulfooxy)butyrate
tetradecylphenyl 3-(hydrogen sulfooxy)butyrate
2-(2-ethoxyethoxy)ethyl 3-(hydrogen sulfooxy)butyrate
2-(2-butoxyethoxy)ethyl 3-(hydrogen sulfooxy)butyrate
fluorodecyl 3-(hydrogen sulfooxy)butyrate
trifluorooctyl 3-(hydrogen sulfooxy)butyrate
pentadecafluorodecyl 3-(hydrogen sulfooxy)butyrate
fluorododecyl 3-(hydrogen sulfooxy)butyrate
2-(N,N-ditallow-N-methylammonium)ethyl 3-(hydrogen sulfooxy)butyrate
3-(N,N-ditallow-N-methylammonium)propyl 3-(hydrogen sulfooxy)butyrate
2-(N-nonyl-N,N-dimethylammonium)ethyl 3-(hydrogen sulfooxy)butyrate
2-(N-sterayl-N,N-dimethylammonium)ethyl 3-(hydrogen sulfooxy)butyrate
2-(N-dodecyl-N,N-dimethylammonium)ethyl 3-(hydrogen sulfooxy)butyrate
hexyl 2-(hydrogen sulfooxy)hexanoate
octyl 2-(hydrogen sulfooxy)hexanoate
nonyl 2-(hydrogen sulfooxy)hexanoate
decyl 2-(hydrogen sulfooxy)hexanoate
dodecyl 2-(hydrogen sulfooxy)hexanoate
tetradecyl 2-(hydrogen sulfooxy)hexanoate
hexadecyl 2-(hydrogen sulfooxy)hexanoate
octadecyl 2-(hydrogen sulfooxy)hexanoate
docosyl 2-(hydrogen sulfooxy)hexanoate
tetracosyl 2-(hydrogen sulfooxy)hexanoate
2-ethylhexyl 2-(hydrogen sulfooxy)hexanoate
2-ethyldecyl 2-(hydrogen sulfooxy)hexanoate
2-ethyldodecyl 2-(hydrogen sulfooxy)hexanoate 2-propyldecyl 2-(hydrogen sulfooxy)hexanoate
2-butyldoecyl 2-(hydrogen sulfooxy)hexanoate
2-octyldodecyl 2-(hydrogen sulfooxy)hexanoate
2-dodecyl hexadecyl 2-(hydrogen sulfooxy)hexanoate
2-tetradecyloctadecyl 2-(hydrogen sulfooxy)hexanoate
2-ethyldecyl 2-(hydrogen sulfooxy)hexanoate
hexenyl 2-(hydrogen sulfooxy)hexanoate
decenyl 2-(hydrogen sulfooxy)hexanoate
dodecenyl 2-(hydrogen sulfooxy)hexanoate
tetradecenyl 2-(hydrogen sulfooxy)hexanoate
hexadecenyl 2-(hydrogen sulfooxy)hexanoate
octadecenyl 2-(hydrogen sulfooxy)hexanoate
docosenyl 2-(hydrogen sulfooxy)hexanoate
tetracosenyl 2-(hydrogen sulfooxy)hexanoate
nonylphenyl 2-(hydrogen sulfooxy)hexanoate
decylphenyl 2-(hydrogen sulfooxy)hexanoate
dodecylphenyl 2-(hydrogen sulfooxy)hexanoate
tetradecylphenyl 2-(hydrogen sulfooxy)hexanoate
2-(2-ethoxyethoxy)ethyl 2-(hydrogen sulfooxy)hexanoate
2-(2-butoxyethoxy)ethyl 2-(hydrogen sulfooxy)hexanoate
fluorodecyl 2-(hydrogen sulfooxy)hexanoate
trifluorooctyl 2-(hydrogen sulfooxy)hexanoate
pentadecafluorodecyl 2-(hydrogen sulfooxy)hexanoate
fluorododecyl 2-(hydrogen sulfooxy)hexanoate
2-(N,N-ditallow-N-methylammonium)ethyl 2-(hydrogen sulfooxy)hexanoate
3-(N,N-ditallow-N-methylammonium)propyl 2-(hydrogen sulfooxy)hexanoate
2-(N-nonyl-N,N-dimethylammonium)ethyl 2-(hydrogen sulfooxy)hexanoate
2-(N-sterayl-N,N-dimethylammonium)ethyl 2-(hydrogen sulfooxy)hexanoate
2-(N-dodecyl-N,N-dimethylammonium)ethyl 2-(hydrogen sulfooxy)hexanoate
hexyl 2-(hydrogen sulfooxy)octanoate
octyl 2-(hydrogen sulfooxy)octanoate
nonyl 2-(hydrogen sulfooxy)octanoate
decyl 2-(hydrogen sulfooxy)octanoate
dodecyl 2-(hydrogen sulfooxy)octanoate
tetradecyl 2-(hydrogen sulfooxy)octanoate
hexadecyl 2-(hydrogen sulfooxy)octanoate
octadecyl 2-(hydrogen sulfooxy)octanoate
docosyl 2-(hydrogen sulfooxy)octanoate
tetracosyl 2-(hydrogen sulfooxy)octanoate
2-ethylhexyl 2-(hydrogen sulfooxy)octanoate
2-ethyldecyl 2-(hydrogen sulfooxy)octanoate
2-ethyldodecyl 2-(hydrogen sulfooxy)octanoate
2-propyldecyl 2-(hydrogen sulfooxy)octanoate
2-butyldoecyl 2-(hydrogen sulfooxy)octanoate
2-octyldodecyl 2-(hydrogen sulfooxy)octanoate
2-dodecyl hexadecyl 2-(hydrogen sulfooxy)octanoate
2-tetradecyloctadecyl 2-(hydrogen sulfooxy)octanoate
2-ethyldecyl 2-(hydrogen sulfooxy)octanoate
hexenyl 2-(hydrogen sulfooxy)octanoate
decenyl 2-(hydrogen sulfooxy)octanoate
dodecenyl 2-(hydrogen sulfooxy)octanoate
tetradecenyl 2-(hydrogen sulfooxy)octanoate
hexadecenyl 2-(hydrogen sulfooxy)octanoate
octadecenyl 2-(hydrogen sulfooxy)octanoate
docosenyl 2-(hydrogen sulfooxy)octanoate
tetracosenyl 2-(hydrogen sulfooxy)octanoate
nonylphenyl 2-(hydrogen sulfooxy)octanoate
decylphenyl 2-(hydrogen sulfooxy)octanoate
dodecylphenyl 2-(hydrogen sulfooxy)octanoate
tetradecylphenyl 2-(hydrogen sulfooxy)octanoate
2-(2-ethoxyethoxy)ethyl 2-(hydrogen sulfooxy)octanoate
2-(2-butoxyethoxy)ethyl 2-(hydrogen sulfooxy)octanoate
fluorodecyl 2-(hydrogen sulfooxy)octanoate
trifluorooctyl 2-(hydrogen sulfooxy)octanoate
pentadecafluorodecyl 2-(hydrogen sulfooxy)octanoate
fluorododecyl 2-(hydrogen sulfooxy)octanoate
2-(N,N-ditallow-N-methylammonium)ethyl 2-(hydrogen sulfooxy)octanoate
3-(N,N-ditallow-N-methylammonium)propyl 2-(hydrogen sulfooxy)octanoate
2-(N-nonyl-N,N-dimethylammonium)ethyl 2-(hydrogen sulfooxy)octanoate
2-(N-sterayl-N,N-dimethylammonium)ethyl 2-(hydrogen sulfooxy)octanoate
2-(N-dodecyl-N,N-dimethylammonium)ethyl 2-(hydrogen sulfooxy)octanoate
didecyl 2-(hydrogen sulfooxy)succinate
dioctyl 2-(hydrogen sulfooxy)succinate
didodecyl 2-(hydrogen sulfooxy)succinate
monodecyl 2-(hydrogen sulfooxy)succinate
monododecyl 2-(hydrogen sulfooxy)succinate
monotetradecyl 2-(hydrogen sulfooxy)succinate
monohexadecyl 2-(hydrogen sulfooxy)succinate
hexadecenyl 2-(hydrogen sulfooxy)succinate
octadecenyl 2-(hydrogen sulfooxy)succinate
tetradecenyl 2-(hydrogen sulfooxy)succinate
dodecenyl 2-hydrogen sulfooxy)succinate
monodecyl 3-(hydrogen sulfooxy)citrate
monododecyl 3-(hydrogen sulfooxy)citrate
monotetradecyl 3-(hydrogen sulfooxy)citrate
monohexadecyl 3-(hydrogen sulfooxy)citrate
monooctadecyl 3-(hydrogen sulfooxy)citrate
didecyl 3-(hydrogen sulfooxy)citrate
didodecyl 3-(hydrogen sulfooxy)citrate
ditetradecyl 3-(hydrogen sulfooxy)citrate The chemistry of sulfoxy ester compounds is known to give mono-, di-, and tri-substituted sulfoxy ester surfactants. The molecules described in this invention can contain a mixture of such, and preferably the mono-substituted sulfoxy esters and disubstituted sulfoxy esters can be used singly or in combination.

While not wishing to be bound by theory, it is believed that enzymes naturally present in the skin will break down molecules of Formula I or that the molecules will be naturally hydrolyzed upon contact with the skin according to the following scheme:

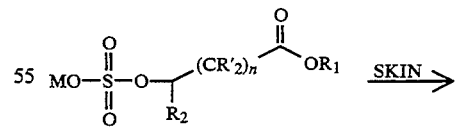

"BENEFIT REAGENTS"
e.g., Hydroxy Acid and/or
Fatty Alcohol

As indicated above, in one aspect of the invention, the invention provides for the use of the novel surfactant molecule in diverse personal product applications ranging from toilet bar soaps to local/body cleaners to toothpaste.

Examples of the molecule in various personal product formulations may be found in the examples section.

PREPARATION OF ESTER SULFATES

The molecules of the invention were obtained essentially through a process in which a desired hydroxy carboxylic acid (or hydroxy acid ester or lactone) was prepared and the molecule thus was then sulfated to obtain the final product.

For example, one hydroxy acid, alkyl lactate, may be prepared by direct esterification or transesterification as taught by Dixon et al., J. Am. Chem. Soc. 72: 1918–1922 (1950) and Holtin et al., Verlag Chemie, 232–238 (1971). Preparation of alkyl alkanoates is described in further detail in the examples.

The preparation of the hydroxy carboxylic acid or hydroxy carboxylic acid ester (including lactone esters) which is to be sulfated does not necessarily result in a pure yield of the hydroxy acid or the hydroxy acid ester and, in fact, unless vacuum distillation is used (which does result in a nearly pure yield), the preparation of the hydroxy acid or the hydroxy acid ester additionally results in the preparation of a free alcohol.

The sulfation of the free alcohol results in the preparation of an alkyl sulfate which, while not a benefit-containing reagent contemplated by the invention, is a useful surfactant (such as sodium dodecyl sulfate (SDS) for example). This is important because it shows that even the free alcohol by-product of the reaction for preparing hydroxy acid or hydroxy acid ester prior to sulfation can be used to prepare a useful, commercial product.

Having obtained the hydroxy acid, the hydroxy acid ester and/or free alcohol (which, as indicated above, can be sulfated to obtain commercial surfactants), sulfation of the molecule is achieved as follows:

First, the sulfation temperature may range from about $-80°$ C. to about $120°$ C., preferably at about $-20°$ to $35°$ C., most preferably about $0°-5°$ C.

As a sulfating agent, a number of sulfating agents such as are known in the art, e.g., sulfonic acid, chlorosulfonic acid, amidosulfonic acid and sulfur trioxide may be used. $SO_3$/pyridine complex may also be used. Other possible sulfating agents are described, for example, in "Sulfation and Related Reactions", Gilbert E. Interscience Publisher, 1965, Chap. VI. pp. 339–383. The preferred agent is chlorosulfonic acid or $SO_3$.

When a hydroxy carboxylic acid ester substrate is to be sulfated, it is generally difficult to sulfate such ester linkages (or other weak linkages). Accordingly, in a preferred embodiment of the invention, sulfation is accomplished under anhydrous conditions. In order to minimize hydrolysis of the ester (or other weak bond) link. In one preferred embodiment, sulfation is done under a nitrogen blanket of atmosphere.

In general, at least about 0.8 to 4 equivalents, preferably 0.8 to 2 equivalents, most preferably 0.8 to 1.2 equivalents of sulfating agents are used.

An acid scavenger may also be used to minimize hydrolyzed by-products. If an acid scavenger is used, preferred scavengers which may be used include pyridine or triethylamine.

Other scavengers which may be used to minimize hydrolysis include weak organic bases such as triethanolamine, inorganic bases such as sodium carbonate or polymeric bases.

The sulfation reaction generally may take from about 5 minutes to 24 hours, preferably 5 minutes to 6 hours, most preferably, 5 minutes to 60 minutes. Preferably the reaction should run no longer than one hour in order to minimize hydrolysis.

Solvents which may be used (although not required) for the sulfation include tetrahydrofuran (THF), hydrocarbon solvents and halocarbons solvents (e.g., chloroform).

Finally, it is preferred to reduce head, e.g., with an ice quench, in order to minimize hydrolysis of both carboxy and sulfate esters.

Table 1 below provides a summary of sulfation reaction using various alkyl alkanoates as a starting reactant:

TABLE 1

Preparation of Alkyl I Sulfooxyalkanoates Sodium Salt $$HO\underset{R_1}{\overset{}{\diagdown}}(CH_2)_n\overset{O}{\overset{\|}{C}}OR_2 \xrightarrow[\text{2) NaOH}]{\text{1) ClSO}_3\text{H}}$$

$$NaO-\overset{O}{\underset{O}{\overset{\|}{\underset{\|}{S}}}}-O\underset{R_1}{\overset{}{\diagdown}}(CH_2)_n\overset{O}{\overset{\|}{C}}OR_2$$

| $R_1$ | n | $R_2$ | Crude Yield | Isolated Yield |
|---|---|---|---|---|
| $CH_3$ | 0 | $C_{10}H_{21}$ | Quantitative | 99%* |
| $CH_3$ | 0 | $C_{12}H_{25}$ | Quantitative | — |
| $CH_3$ | 0 | $C_8H_{17}$ | ca. 60% | — |
| $CH_3$ | 1 | $C_{10}H_{21}$ | Quantitative | 97%* |
| $CH_3$ | 1 | $C_{12}H_{25}$ | Quantitative | 99%* |
| $(CH_2)_5CH_3$ | 0 | $C_{10}H_{21}$ | Quantitative | 62% |

*>90% Pure by Hyamine Titration, <1% of Cl

Sulfation results in the formation of a hydrogen sulfooxy acid or the ester thereof (or of an alkyl sulfate if the substrate was a free alcohol by-product of the reaction in which the hydroxy acid and the ester were prepared). The molecule is then neutralized with inorganic or organic bases (e.g., sodium bicarbonate, sodium hydroxide or triethanolamine). At least partial neutralization is required. Preferred bases used for neutralization include sodium and potassium salts and triethanolamine.

Among alkyl sulfooxyalkonates produced using these techniques are decyl 2-sulfooxypropionate (DSP), dodecyl 2-sulfooxypropionate (LSP), decyl 3-sulfooxybutyrate (DSB), dodecyl 3-sulfooxybutyrate (LSB), decyl 2-sulfooxyoctanoate (DSO) and octyl-2-sulfooxypropionate (OSP). These molecules are set forth below:

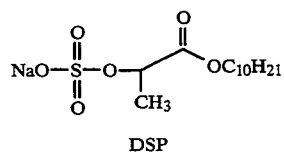

DSP

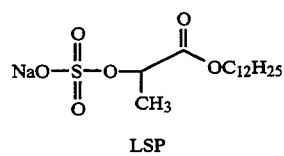

LSP

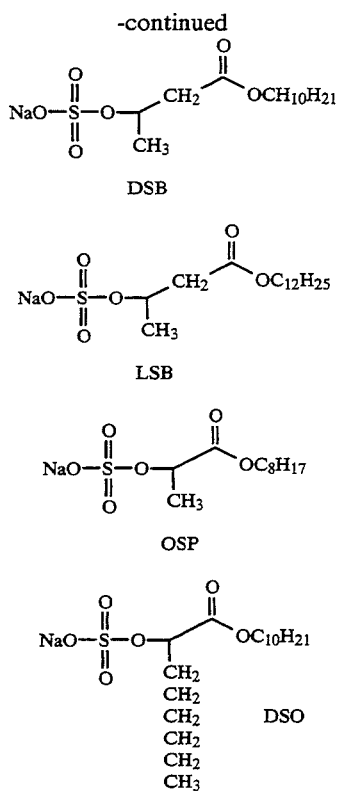

Preparation of various alkanoates is set forth in Table II below:

EXAMPLE 1

General Procedures and Techniques Used

Boiling points were measured during vacuum distillation and are un-corrected. Proton magnetic resonance ($^1$H NMR) spectra were recorded on a Bruker 200 MHz FT spectrometer or Varian 300 MHz FT spectrometer or Varian T-60 spectrometer. Carbon magnetic resonance spectra ($^{13}$C NMR) were recorded on a Bruker 200 FT (50 MHz) spectrometer. Proton and carbon chemical shifts are reported in parts per million downfield from tetramethylsilane as an internal standard or other silylated standard. Coupling constants (J value) are given in Hertz (Hz) and spin multiplicities are indicated as follows: s (singley), d (doublet), t (triplet), q (quartet), m (multiplet), or br (broad). The deuterated NMR solvents contain 99.0–99.8% deuterium in the indicated position and these solvents were purchased from Aldrich Chemical Company and from Cambridge Isotope Laboratories. Infrared spectra (IR) were recorded on a Perkin-Elmer model 298 spectrometer or a Nicolet 5SX FT IR spectrometer using a NaCl cell. Peak positions are listed as vs (very strong), s (strong), m (medium), w (weak) or b(broad).

High resolution fast atomic bombardment mass spectra (FAB M.S.) were obtained on a hybrid VG 705 EQ (magnetic sector, quadropole hybrid instrument) as Georgia Tech Institute University, Atlanta, Ga., USA. FAB M.S. were obtained on a tandem quadropole Finnigan MAT TSQ70 instrument. Gas chromatography (GC) was performed using a model 5840A purchased from Hewlett Packard with a 5% OV101 methyl silica packed column (80/100 chromosorb 6"×⅛"). The GC parameters were set as follows: Inj. temp.=250° C., initial column. temp.=70° C., final column, temp.=250° C., rate=10° C./minute.

Chlorosulfonic acid was purchased from Aldrich Chemical Chemical and were used as received. Alcohols (octanol, decanol, dodecanol alcohol, tetradecyl alcohol) were reagent grade quality and were used as received. Lactic acid, 3-hydroxy butyric acid; β-butyrolactone and hydroxycaproic acid were received from Aldrich and were used as received. Hydroxyoc-

TABLE II

PREPARATION OF ALKYL ALKANOATE

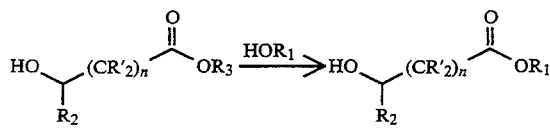

| Entry | R$_2$ | R' | n | R$_3$ | R$_1$ | Dist. Yield | Purity by GC |
|---|---|---|---|---|---|---|---|
| 1 | CH$_3$ | H | 0 | H | —(CH$_2$)$_7$CH$_3$ | 36–65% | 96.0% |
| 2 | CH$_3$ | H | 0 | H | —(CH$_2$)$_9$CH$_3$ | 12–58% | 95.0% |
| 3 | CH$_3$ | H | 0 | CH$_3$ | —(CH$_2$)$_7$CH$_3$ | 44% | 95.0% |
| 4 | CH$_3$ | H | 0 | CH$_3$ | —(CH$_2$)$_9$CH$_3$ | 45–62% | >99.0% |
| 5 | CH$_3$ | H | 0 | CH$_3$ | —(CH$_2$)$_{11}$CH$_3$ | 62% | 100.0% |
| 6 | CH$_3$ | H | 1 | H | —(CH$_2$)$_9$CH$_3$ | 58% | 89.0% |
| 7 | CH$_3$ | H | 1 | H | —(CH$_2$)$_{11}$CH$_3$ | 60% | 91.0% |
| 8 | (CH$_3$)$_2$ | H | 0 | H | —(CH$_2$)$_9$CH$_3$ | 65% | 99.5% |
| 9 | —(CH$_2$)$_3$CH$_3$ | H | 0 | H | —(CH$_2$)$_9$CH$_3$ | 49% | 96.0% |
| 10 | —(CH$_2$)$_5$CH$_3$ | H | 0 | H | —(CH$_2$)$_9$CH$_3$ | 77% | 99.0% |
| 11 | β-Butylrolactone | | | — | —(CH$_2$)$_{11}$CH$_3$ | 89%* | 80.0% |
| 12 | CH$_3$ | H | 0 | H | —(CH$_2$)$_{13}$CH$_3$ | 70%* | 69.0% |
| 13 | H | H | 0 | CH$_3$ | —(CH$_2$)$_{11}$CH$_3$ | 98%* | 78.0% |

*GC Yield.

As indicated above, free alcohols (e.g., fatty acid alcohols) may be a by-product of the preparation of the alkyl alkanoate (especially if no vacuum distillation is used). These by-products may be sulfated to produce commercial alkyl sulfates such as SDS.

The following examples are intended to illustrate the invention and facilitate its understanding and are not meant to limit the invention in any way.

tanoic acid (HCA) were purchased from Lancaster Synthesis and was used as received.

EXAMPLE 2

Preparation of Octyl 2-Sulfoxypropionate Sodium Salt

Preparation of Octyl Lactate by Transesterification

A 500 mL one neck round bottom flask equipped with a distillation apparatus and nitrogen inlet/outlet was charged with 100.0 g (0.85 moles) of ethyl lactate, 220.49 g (1.69 moles) of octyl alcohol and 0.42 g of sulfuric acid. The reaction was refluxed for 8 hours and ethanol was collected as formed. The acid was neutralized by washing three times with 100 mL saturated sodium bicarbonate solution. The organic layer was collected and dried over magnesium sulfate. Excess octyl alcohol was removed by high vacuum distillation, and three fractional distillations led to 75.0 g (44% yield) of clear colorless oil. According to GC, the product is 95% pure.

B.P.=93.5°-94.5° C./0.45 mm (lit B.P.=87° C./1.0 mm).

GC (Rt): 11.8.

IR (neat, in cm$^{-1}$): 3420 (br.m), 1737.4 (s), 1480 (m), 1212 (m), 1131 (s).

$^1$H NMR (200 MHz FT, CDCl$_3$ with TMS): $\delta$4.4 (q,J=6.8 Hz, 1H), 4.2 (t,J=6.5 Hz, 2H), 3.3 (—OH, br.s, 1H), 1.7 (br.t, J=6.5 Hz, 2H), 1.4 (d,J=6.8 Hz, 3H), 1.3 (br.s, 10H), 0.9 (br. t,J=6.5 Hz, 3H).

$^{13}$C NMR (50 MHz, CDCl3 in ppm): 175.9, 66.8, 65.8, 31.85, 29.3, 29.23, 28.64, 25.87, 22.71, 20.5, 14.1.

Preparation of Octyl Lactate by Direct Esterification

A 2liter one neck round bottom flask equipped with a Dean Stark trap, condenser and nitrogen inlet/outlet was charged with 150.0 g (1.67 moles) lactic acid, 293.0 g (2.25 moles) octyl alcohol, 6 ml sulfuric acid and 500 ml toluene. Mixture was heated to 130° C. for 6 hours and water was collected as the reaction proceeded. The acid was neutralized by washing three times with 50 ml saturated sodium bicarbonate solution. The organic layer was collected and dried over magnesium sulfate. Octyl lactate was distilled under high vacuum to yield 119.9 g (35.6% yield) of clear colorless liquid. According to GC the product is 96.2% pure.

Spectral data identical as described above.

Preparation of Octyl 2-Sulfooxypropionate Sodium Salt from Octyl Lactate

A 50 mL Schlenk flask equipped with a spin bar was charged with 1.73 g (14.9 mmole) of ClSO$_3$H. The reaction flask was cooled to ca. 0° C. in an ice water bath under a nitrogen atmosphere, and octyl lactate (2.5 g, 12.4 mmole) was slowly added. After addition was completed, the reaction was maintained at 0° C. and was stirred for 15 minutes. A solution of sodium hydroxide in deionized water/ice was added, and the pH was adjusted to ca. 7.0. The water layer was collected and lyophilized to give 4.6 g of a crude white product. The white solid was not further purified. Proton NMR indicated the presence of the hydrolyzed product, lactate (ca. 45%).

IR (nujol, in cm$^{-1}$): 1735 (s), 1255 (br.s), 1220 (br.s), 1120 (s), 1060 (s), 1030 (s), 950 (s).

$^1$H NMR (100 MHz FT, D$_2$O), $\delta$4.65 (apparent q, 1H), 4.0 (m, 2H), 1.5 (br.m, 2H), 1.35 (d,J=6.9 Hz, 3H), 1.15 (br.s, 10H), 0.7 (br.5, 3H).

Low Resolution FAB M.S. (from glycerol/H$_2$O, (%) relative intensity): m/z 327 (M=Na).

EXAMPLE 3

Preparation of Decyl 2-Sulfooxypropionate Sodium Salt

Preparation of Decyl Lactate by Transesterification

A 250 mL round bottom flask equipped with a spin bar and a distillation column was charged with 100 g (0.96 moles) of methyl lactate, 304.1 g (1.92 moles) of decanol, and 500 mg of H$_2$SO$_4$. The reaction was heated until methanol formation ceased. The reaction was then neutralized with 0.1N NaOH (100 mL) and extracted. The organic layer was dried over MgSO$_4$, filtered, and dried in vacuo to give 400 g of crude mixture. The fractional distillation was carried out 3 times to give 98.5 g (45% yield, 100% pure by GC) of a clear colorless oil.

B.P=122°-124° C./2.0 mm (lit. B.P.=109° C./1.0 mm).

GC (R$_t$): 14.61.

IR (neat, in cm$^{-1}$): 3467.3 (br.s), 1737.5 (s), 1465.5 (s), 1264.9 (s), 1213.02 (s), 1131.2 (s), 1044 (m).

$^1$H NMR (200 MHz FT. CDCl$_3$with TMS): $\delta$4.4 (q,J=6.9 Hz, 1HO, 4.15 (dt,J=0.9 Hz,J=6.5 Hz, 2H), 3.1 (br.s, 1H), 1.7 (br.s 6.5 Hz, 2H), 1.45 (d,J=6.9 Hz, 3H), 1.3 (br.s, 14H), 0.8 (br.t, 6.6 Hz, 3H). $^{13}$C NMR (50 MHz, CDCl$_3$, in ppm): 175.6, 66.7, 65.5, 31.7, 29.4, 29.3, 29.1, 29.0, 28.4, 25.7, 22.6, 20.3, 13.9.

Preparation of Decyl Lactate by Direct Esterification

A 500 mL one neck round bottom flask equipped with a Dean Stark trap, condensor and nitrogen inlet/outlet was charged with 22.52 g (0.75 moles) lactic acid, 47.46 g (0.98 moles) decyl alcohol, 3 ml sulfuric acid and 220 mL toluene. The mixture was heated to 145° C. for 20 hours and water was collected as the reaction proceeded. The acid was neutralized by washing three times with 50 ml saturated sodium bicarbonate solution. The organic layer was collected and dried over magnesium sulfate. Decyl lactate was distilled under high vacuum to yield 24.03 g (12.4% yield) of clear colorless liquid. According to GC the product is 97.78% pure.

Preparation of Decyl 2-Sulfooxypropionate Sodium Salt from Decyl Lactate

A 50 mL Schlenk flask equipped with a spin bar was charged with 2.45 g (21 mmole) of ClSO$_3$H. The reaction flask was cooled to ca. 0° C. in an ice/water bath under a nitrogen atmosphere and decyl lactate (4.6 g, 20 mmole) was slowly added. After addition was complete, the reaction was maintained at 0° C. and was stirred for 15 minutes. A solution of sodium hydroxide in deionized water/ice was added, and pH was adjusted to 7.0. This water solution was extracted with ether to remove any organic residue. The water layer was collected and lyophilized t give 8.7 g of a crude white product. The white solid was washed with warm ethanol, filtered and dried to give 6.7 g (100% yield) of white solid.

IR (nujol, in cm$^{-1}$): 1740 (s), 1255 (br.s), 1220 (br.s), 1120 (s), 1060 (s), 1030 (s), 990 (m), 950 (s).

$^1$H NMR (100 MHz FT, D$_2$O) $\delta$4.65 (apparent q,J=6.9 Hz, 1H), 4.0 (m, 2H), 1.55 (br.s, 2H), 1.35 (d,J=6.9 Hz, 3H), 1.15 (br.s, 16H), 0.9 (br.s, 3H).

$^{13}C$ NMR (50 MHz, D$_2$O with TSP in ppm): 175.7, 75.34, 68.73, 34.8, 32.6, 32.5, 32.3, 31.1, 28.67, 25.45, 20.9, 16.6.

High Resolution FAB M.S. (from glycerol/H$_2$O, (%) relative intensity): m/z 355 (M+Na, 100%).

EXAMPLE 4

Preparation of Dodecyl 2-Sulfooxypropionate Sodium Salt

Preparation of Dodecyl Lactate

A 1 liter one neck round bottom flask equipped with a distillation apparatus and nitrogen inlet/outlet was charged with 200.0 g (2.69 moles)ethyl lactate, 536 g (3.4 moles) dodecyl alcohol and 0.85 g sulfuric acid. The reaction was refluxed for 12 hours and ethanol was collected as formed. The acid was neutralized by washing three times with 100 ml saturated sodium bicarbonate solution. The organic layer was collected and dried over magnesium sulfate. Excess dodecyl alcohol was removed by high vacuum distillation leaving 271.8 g (62.1% yield) of clear viscous light gold colored oil. According to GC and the product is 100% pure.

GC (Rt): 17.14.

IR (near, in cm$^{-1}$): 3460 (br.s), 1735 (s) 1470 (s), 1380(m), 1260 (br.s), 1210 (br.s), 1130 (s), 1040 (m).

$^1$H NMR (200 MHz FT, CDCl$_3$ with TMS): δ4.3 (m, 1H0, 4.2 (dt,J=6.5 Hz,J=1.4 Hz, 2H) 3.1 (d,J=6.3 Hz, 1H), 1.7 (br.m, 2H), 1.4 (d,J=6.9 Hz, 3H), 1.26 (br.s, 18H), 0.9 (br.t, J=6.7 Hz,3H)

$^{13}C$ NMR (50 MHz, CDCl$_3$ with TMS, in ppm): 176.5, 67.28, 66.32, 32.47, 30.18, 30.1, 30.05, 29.9, 29.74, 29.6, 29.09, 26.34, 23.24,20.97, 14.65.

Preparation of Decyl 2-Sulfooxypropionate Sodium Salt from Dodecyl Lactate

A 100 ml round bottom flask equipped with a spin bar was charged with 6.06 g (52 mmole) of ClSO$_3$H.

The reaction flask was cooled to ca. 0° C. in an ice/water bath and 12.9 g (50 mmole) of dodecyl lactate was slowly added. The addition was slow and reaction temperature was maintained at ca. 0° C. After addition was complete, the reaction was stirred for 15 minutes. To a beaker filled with a solution of sodium hydroxide (2.08 g) in deionized water/ice was added the crude reaction mixture. The pH was brought to ca. 7.0. This water solution was extracted with ether to remove any organic residual. The water layer was collected and lyophilized to give 20.1 g of a white solid. From M.S. and $^1$H NMR, a trace of unreacted dodecyl lactate is present in the reaction mixture.

IR (nujol, in cm$^{-1}$): 1730 (s),1250 (vs), 1220 (br.s), 1200 (s), 1130 (vs), 1100 (br.s), 1070 (s), 1030 (s), 965 (s).

$^1$H NMR (100 MHz FT, D$_2$O) δ4.65 (apparent q, 1H), 3.9 (br.s, 2H), 1.45 (br.s, 2H), 1.35 (d,J=7.2 Hz, 3H), 1.15 (br.s, 20H), 0.9 (br.s, 3H).

$^{13}C$ NMR (50 MHz, D$_2$O with TSP in ppm): 175.2, 74.9, 68.27, 34.48, 32.5, 32.05, 30.84, 28.35, 25.09, 25.45, 22.55, 21.53, 20.5, 16.2.

High Resolution FAB M.S. (from glycerol/H$_2$O, (%) relative intensity): m/z (M+Na, 100%).

EXAMPLE 5

Preparation of Decyl 3-Sulfooxybutyrate Sodium Salt

Preparation of decyl 3-Hydroxybutyrate

A 100 ml of one neck round bottom flask equipped with a Dean Start trap, condensor and nitrogen inlet/outlet was charged with 20.8 g (0.20 moles) 3-hydroxybutyric acid, 63.3 g (0.40 moles) decyl alcohol, and 0.1 g sulfuric acid. The mixture was heated to 140° C. for 8 hours and water was collected as the reaction proceeded. The acid was neutralized by washing three times with 50 ml saturated sodium bicarbonate solution. The organic layer was collected and dried over magnesium sulfate. Excess decyl alcohol was removed by high vacuum distillation to yield 28.3 g (58% yield) of clear viscous colorless oil. According to GC the product is 89.4% pure.

GC (R$_t$): 15.6.

IR (near, in cm$^{-1}$): 3450 (br.s), 1730 (s), 1470 (s), 1170 (s).

$^1$H NMR (200 MHz FT, CDCl$_3$ with TMS) δ4.3 (m, 1H), 4.2 (t,J=6.7 Hz, 2H), 3.5 (—OH,d, J=3.8 Hz), 2.4 (d,J=5.9 Hz, 2H), 1.9–1.5 (br.s, 21H), 0.9 (br.t, J=6.7 Hz, 3H).

$^{13}C$ NMR (50 MHz, CDCl$_3$ with TMS, in ppm): 170.15, 62.14, 61.59, 40.42, 29.3, 26.93, 26.8, 26.71, 26.65, 25.96, 23.3, 20.08, 19.92, 11.48.

Preparation of Decyl 3-Sulfooxybutyrate Sodium Salt from Decyl 3-Hydroxybutyrate A 100 mL round bottom flask equipped with a spin bar was charged with 6.8 g (58.2 mmole) of ClSO$_3$H. The reaction flask was cooled to ca 0° C. in an ice/water bath and 14.2 g (58.2 mmole) of decyl 3-hydroxybutyrate was slowly added to ca. 0° C. After addition was complete, the reaction was stirred for 30 minutes. To a beaker filled with a solution of sodium hydroxide (4.6 g) in deionized water/ice was added the crude reaction mixture. The pH was brought to 7.0. This water solution was extracted with ether to remove any organic residual. The water layer was collected and lyophilized to give 24.7 g of a white solid. The crude material was added to 2 L beaker equipped with spin bar and 1.2 L of absolute ethanol. The mixture was stirred at room temperature for 48 hours. The white solid was filtered and ethanol was concentrated to give sticky white solid which was dissolved in water and lyophilized to give (98% yield) of white powder.

IR (nujol, in cm$^{-1}$): 1730 (s), 1300 (s), 1255 (s), 1200 (s), 1185 (s), 1135 (s), 1080 (s), 930 (s).

$^1$H NMR (100 MHz FT, D$_2$O with TSP in ppm) δ4.6 (apparent q overlapped with DHO peak, 1H), 3.9 (t, J=6.5 Hz, 2H), 2.6 (dd, J =6.4 Hz, J=15.3 Hz, 1H), 2.4 (dd, J=15.3 Hz, J=6.4 Hz, 3H), 1.5 (br.t, 2H), 1.2 (d, J=6.4 Hz, 3H), 1.15 (br.s, 16H), 0.9 (br.t, J=6.4 Hz, 3H).

$^{13}$CNMR (50 M Hz, D$_2$O with TSP in ppm: 1784.62, 75.52, 67.78, 43.94, 34.43, 32.15, 31.89, 30.84, 28.4, 25.11, 22.66, 16.32.

High Resolution FAB M.S. (from glycerol/H$_2$O , (%) relative intensity): m/z 369 (M+Na, 100%).

EXAMPLE 6

Preparation of Dodecyl 3-Sulfooxybutyrate Sodium Salt

Preparation of Dodecyl 3-Hydroxybutyrate

A 500 mL one neck round bottom flask equipped with a Dean Stark trap, condenser, and a nitrogen inlet/outlet was charged with 72.0 g (69 mmole) of 3-hydroxybutyric acid, 268.5 g (1.45 mole) of dodecyl alcohol, and 0.36 g of sulfuric acid. The mixture was heated to 120° C. for 48 hours and water was collected as the reaction proceeded. The acid was neutralized by washing three times with 100 mL saturated NaHCO3 solution. The organic layer was collected and dried over MgSO4 and concentrated. Excess dodecanol was removed by high vacuum distillation to yield 117.65% (60% yield) of clear oil (91% pure by GC).

GC (Rt): 18.17.

IR (near, in cm$^{-1}$): 3450 (br.s), 1730 (s), 1465 (s), 1375 (m), 1295 (s), 1180 (s), 1080 (m).

$^1$H NMR (200 MHz, CDCl3 with TMS) $\delta$4.15 (m, 1H), 4.1 (t, J=6.7 Hz, 2H), 3.15 (br.s, —OH, 1H), 2.4 (apparent t, J=4 Hz, 2H), 1.6 (br.m, 2H), 1.25 (br.s, 20H), 0.9 (bt. t, J=6.8 Hz, 3H).

Preparation of Dodecyl 3-Sulfooxybutyrate Sodium Salt from Dodecyl 3-Hydroxybutyrate A 50 mL Schlenk flask equipped with a spin bar and addition funnel was charged with 6.4 g (55 mmole) of ClSO3H. The reaction flask was cooled to ca. 0° C. in an ice/water bath and 13.6 g (50 mmole) of dodecyl hydroxybutyrate was slowly added. The addition was slow and reaction was maintained at ca. 0° C. After addition was complete, the reaction was stirred for 15 minutes. To a beaker filled with a solution of sodium hydroxide (2.2 g) in deionized water/ice was added the crude reaction mixture. The pH was brought to 7.0. This water solution was extracted with ether to remove any organic residual. The water layer was collected and lyophilized to give 20.6 g of a white solid. The white solid was dissolved in warm ethanol, filtered and ethanol was concentrated to give stick white solid which was dissolved in water and lyphilized to give 18.2 g (98% yield) of white powder.

IR (nujol, in cm$^{-1}$): 1735 (s), 1300 (m), 1255 (vs), 1200 (s), 1200 (vs), 1180 (vs), 1080 (s), 1030 (s).

$1^H$ NMR (300 MHz FT,D2O with TSP) $\delta$4.8 (apparent q, J=6.6 Hz, 1H), 4.2 (m,diastereotopec 2H), 1.68 (br.t, J=6.6 Hz, 2H), 1.5 (d, J=7.2 Hz, 3H), 1.3 (br.s, 20H), 0.9 (br.t, J=6.9 Hz, 3H).

$^{13}$C NMR (50 MHz, D2O with TSP in ppm) 174.6, 75.5, 67.85, 44.1, 34.7, 32.66, 32.59, 32.23, 27.33, 25.35, 22.94, 21.43, 16.5.

High Resolution FAB M.S. (from glycerol/H2O, (%) relative intensity): m/z 397 (M+Na, 100%).

EXAMPLE 7

Preparation of 2-Sulfooxyoctanoate

Preparation of Decyl 2-Hydroxyoctanoate

A 250 mL one neck round bottom flask equipped with a Dean Stark trap, condensor and nitrogen inlet/outlet was charged with 20.0 g (0.12 moles) 2-hydroxyoctanoic acid, 79.0 g (0.50 moles) decyl alcohol, and 624 mg sulfuric acid. The mixture was heated to 140° C. for 8 hours and water was collected as the reaction proceeded. The acid was neutralized by washing three times with 50 ml saturated sodium bicarbonate solution. The organic layer was collected and dried over magnesium sulfate. Excess decyl alcohol was removed by high vacuum distillation to yield 28.99 g (77.3% yield) of clear pale yellow liquid. According to GC the product is 95.0% pure.

GC (Rt): 20.0.

IR (neat, in cm$^{-1}$): 3500 (s), 1735 (s), 1470 (s), 1210 (s) 1120 (s), 1090 (s).

1H NMR (200 MHz FT, CDCl3 with TMS): $\delta$4.2 (m, 3H), 3.4 (—OH, br.s, 1H), 1.7 (m, 4H), 1.27 (br.s, 22H), 0.9 (2t, J=6 Hz, 6H).

$^{13}$C NMR (50 MHz, CDCl3 with TMS, in ppm): 175.4, 70.21, 65.2, 34.1, 31.67, 31.3, 29.31, 29.09, 28.83, 28.7, 28.5, 28.36, 25.64, 24.5, 22.44, 22.35, 13.78, 13.73.

Preparation of 2-Sulfooxyoctanoate from Decyl 2-Hydroxyoctanoate

A 50 mL Schlenk flask equipped with a spin bar and addition funnel was charged with 1.4 g (12 mmole) of ClSO3H. The reaction flask was cooled to ca. 0° C. in an ice/water bath and 3.0 g (10 mmole) of decyl hydroxyoctanoate was slowly added. The addition was slow and reaction was maintained at ca. 0° C. After addition was complete, the reaction was stirred for 15 minutes. To a beaker filled with a solution of sodium hydroxide in deionized water/ice was added the crude reaction mixture. The pH was brought to 7.0. The crude mixture was lyophilized to give 4.8 g of a white solid. The solid was not readily soluble in water or alcohols (methanol and ethanol). The white solid was washed with cold water and a white stick solid was filtered to give 2.45 g (62% yield) of product after drying.

IR (nujol, in cm$^{-1}$): 1745 (s), 1280 (s), 1215 (s), 1140 (s), 970 (s), 930 (s).

Low Resolution M.S.: m/z 425 (M+Na+).

EXAMPLE 8

Critical Micelle Concentrated of Sulfoxy Ester as Measure of Surfactancy

Due to energetic reasons, surfactants strive to reduce the contact of their hydrophobic chains in water. At the water/air interface, surfactants adsorb with their hydrophobic chains on the water surface. The adsorption of surfactants results in the lowering of surface tension (Gibb's law). Plotting the interfacial tension against the logarithm of the concentration of the surfactants, one can determine critical micelle concentration (CMC).

The micelle formation property which surfactant active solutes have of forming colloidal-sized clusters in solutions is an important phenomena because it is an interfacial phenomena important for defining detergency and solubilization. Specifically, the critical micelle concentration (CMC) is the concentration at which surfactant creates micelles.

The value of the critical micelle concentration was determined by surface tension using the Wilhemy plate method. The comparison was a comparison between one of the alkyl sulfooxy esters of the invention(DSB) and a common commercial anionic surfactant (SDS). The results of the CMC calculations are represented in Table 3 below:

TABLE 3

| Critical Micelle Concentration of Some Surfactants in Aqueous Media | | | |
|---|---|---|---|
| Compound | Solvent | Temperature (°C.) | CMC(mM) |
| Sodium Laurylsulfate (SDS) | H2O | 40 | 8.6* |
| Sodium Decyl 3-Sulfooxybutyrate (DSB) | H2O | 45 | 0.46 |

*as reported at 40° C. by Flockhart, J. Colloid Sci., 16:484 (1961). The minimum surface tension for DSB was about 30 dyne/cm.

As can be observed from Table 3, the critical micelle concentration (i.e., concentration at which surfactant creates micelles) is much lower for DSB than SDS indicating that DSB is much more surface active. While not wishing to be bound by theory, it is believed that lower CMC values suggest that lower amounts of DSB need be used to obtain the same surfactancy benefits.

Further, while again not wishing to be bound by theory, the art seems to indicate that as the CMC gets lower, the surfactant is more mild.

EXAMPLE 9—Comparison of Krafft Point

The temperature at and above which surfactants begin to form micelles instead of precipitates is referred to as Krafft point (Tk) and at this temperature the solubility of an ionic surfactant becomes equal to its CMC. The micelle formation will increase the solubility.

The Krafft point for DSB was measured to be less than 0° C. The surfactant showed a lower Krafft point compared to corresponding surfactant which posses similar hydrophilic group (i.e., SDS). While not wishing to be bound by theory, it is believed that the effect of substitution of ester group on the hydrocarbon chain may result in an increase in the solubility.

Lower Krafft point may result in additional benefits depending on the desired specifications of the formulation in which the surfactant is being used. For example, surfactants with lower Krafft points are more stable in aqueous systems. In addition, it is easier to formulate such surfactants in multi-electrolyte systems since they will be more tolerant to salt.

EXAMPLE 10

Foam Ability of Alkyl Sulfooxyalkanoates

Foam is an important attribute in many consumer products (e.g. cosmetic products). Foam is one of the dominant factors that determines the commercial value of products such as shampoo, soap, etc. Also, acceptability of many consumer products is closely related to the quality and texture of the foam they produce (psychological aspect).

Since most of the foaming data on surfactants is typically obtained by the Ross-Miles method (Ross, J. and Miles G. D., Am. Soc. for Testing Material Method (D 1173-53), Philadelphia, Pa. (1953); Oil and Soap, 62:1260 (1958)), the foaming ability of these surfactants was also acquired using this method.

In the Ross-Miles method, 200 mL of a solution of surfactant contained in a pipette of specified dimensions with a 2.9-mm-i.d. orifice is allowed to fall 90 cm onto 50 mL of the same solution contained in a cylindrical vessel maintained at a given temperature (often 60° C.) by means of a water jacket. The height of the foam produced in the cylindrical vessel is read immediately after all the solution has run out of the pipette (initial foam height) and then again after a given amount of time (generally, 5 min).

Using this method, the foam production (measured initially) and foam stability (the height after 10 minutes) are reported. All of the foaming was achieved at 45° C. in water with 0 ppm hardness. The foam height is represented in mm as illustrated in Table 4.

TABLE 4

| | Ross-Miles Foam Height Test | | | |
|---|---|---|---|---|
| | Initial Height | | Final Height (after 10 minutes) | |
| Compound | 0.05% | 0.1% | 0.05% | 0.1% |
| DSB | negligible | 109 | 0 | 36 |
| LSB | 141 | —* | 84 | —* |
| DSP | negligible | 143 | negligible | negligible |

TABLE 4-continued

| | Ross-Miles Foam Height Test | | | |
|---|---|---|---|---|
| | Initial Height | | Final Height (after 10 minutes) | |
| Compound | 0.05% | 0.1% | 0.05% | 0.1% |
| LSP | 139 | 177 | 124 | 153 |

*not measured

As shown in Table 4, DSB produced negligible foam at a lower concentration (0.05% active) but gave a respectable but apparently unstable foam at 0.1% active solution. However, by adding two more methylene groups onto the hydrophobe chain (LSB), we obtained a respectable foam even at a lower concentration. It appears that the foam increases with an increase in the number of carbon chain.

As can be observed from Table 4, at least some of the alkylsulfooxy alkanoates of the invention (i.e., LSB and LSP) show good foaming at concentrations as low as 0.05 while all showed good foaming at concentrations of 0.1%.

EXAMPLE 11

Harness Sensitivity Test

The calcium ion stability of alkyl sulfooxyalkanoates was measured by a modified Hart method (Witkes, et al. J. Ind. Eng. Chem., 29, 1234–1239 (1937). The surfactant solution was titrated with a calcium ion solution. The endpoint was determined by visual observation of the cloudiness of the surfactant solution.

Many surfactants like fatty soap are known to chelate to calcium ion to form calcium salts which are usually insoluble in aqueous medial. This will lead to the loss of their surfactant properties. Calcium "insensitive" surfactants have unique advantageous properties for many applications such as a formulation for a liquid cleanser. In the case of the sulfate analogs, we noticed that a large amount of calcium ion was added up before precipitation was seen. The LSP and LSB, we did not reach the precipitation limit even at levels well over an order of magnitude higher than the precipitate limit for sodium dodecyl sulfate (SDS). The calcium ion stability results are represented in Table 5.

TABLE 5

| Calcium Ion Sensitivity Test | | |
|---|---|---|
| Compound | Head Group | $Ca^{+2}$ Required for ppt |
| Sodium dodecylsulfate (SDS) | sulfate | 120 ppm |
| Sodium decyl 3-sulfooxybutyrate (DSB) | sulfate | >1550 ppm |
| Sodium lauryl 3-sulfooxybutyrate (LSB) | sulfate | >2500 ppm |
| Sodium decyl 2-sulfooxypropionate (SDSP) | sulfate | ca. 2126 ppm |
| Sodium dodecyl 2-sulfooxypropionate (SLSP) | sulfate | >2500 ppm |
| Sodium decyl 3-sulfopropionate (SDSfP) | sulfonate | 650 ppm* |
| Sodium dodecyl 3-sulfopropionate (SLSfP) | sulfonate | 160 ppm* |
| Sodium lauryl isethionate (SLI) | sulfonate | 51 ppm |

*Value measured by Hikato et al., Bull of Chem. Soc., Japan, 43:158 (1970)

A comparison of the calcium ion sensitivity of LSB and DSB showed that the DSB was slightly less sensitive than LSB. These compounds differ by the number of carbon atoms in their alkyl chain. A similar trend is seen with propionate analogs. Interestingly, Hikota, et al., observed a reverse relationship in his alkyl sulfoalkanoates (sulfonates not sulfates). The calcium ion stability of the surfactant decreased with an increase in the number of carbon atoms. A similar relationship was also seen in SLI analogs (Hikots et al., *Bull of Chem. Soc. Japan*, 43: 158–161 (1970)).

In general, it can be seen that the alkyl sulfooxyalkanoates used in the compositions of the invention are much less calcium sensitive that corresponding sulfate analogs or than the commercially available SDS. This offers a clear advantage in terms of the ability to formulate and use the novel surfactants of the invention in hard (i.e., calcium containing) water.

EXAMPLE 12

In Vitro "Mildness" Test

Assessing Mildness

Many factors have been reported to have an influence on skin irritation such as removal of skin lipids, loss of naturally occuring hygroscopic materials in the stratum corneum, adsorption, protein denaturation, and epidermial lyposomal injury. Although there are many hypotheses regarding skin irritation, it is generally believed that surfactants become irritants because they penetrate the stratum corneum which is a "barrier" and then react with the inner cells of the epidermis.

Traditionally, the study of percutaneous absorption has focused on measuring the diffusion of chemicals (e.g. surfactants through stratum corneum). Diffusion through an organ as complex as skin and its associated adnexal appendages is challenging to measure, model, and predict. Another challenge of cutaneous metabolism is to assess the irritating potential, toxicity, and therapeutic potential of the penetrating compounds.

In vivo, the skin metabolism and percutaneous absorption are very difficult to measure. Finding adequate detection methods and setting up proper experiments are not easy tasks. In vitro studies however are used because of the simplicity of the experimental conditions. We can also minimize or eliminate the use of animals.

We have obtained information on mildness potentials of the surfactant by carrying out in vitro tests which have been demonstrated to correlate well with in vivo tests.

In Vitro Protein Interaction Test

Van Scott and Lyon (Van Scott et al., J. Invest. Dermatol., 21:199–203 (1953)) concluded from their work that protein denaturation was an important mechanism in the production of dermatitis. Bohn (Blohm, S. G., Acta. Derm. Venerol., 37:269–275 (1957)) showed the effect of denaturating a purified protein (ovalbumin) system using sodium dodecyl sulfate (SDS). This type of demonstration showed a relationship between skin irritation and protein denaturation effects of surfactants.

An in vitro "Zein dissolution test" may be used to measure mildness. Specifically, the lower the amount of zein protein dissolved, the milder the surfactant is. Conversely, the more zein dissolved, the more irritating the surfactant is. SDS, which is known to be an irritating surfactant, dissolved 85% of the zein as seen in table 6. By contrast, the amount of zein dissolved by the alkyl sulfooxy alkanoates used in the compositions of the invention was equivalent to that dissolved by SLI, a known mild active ingredient.

TABLE 6

Zein Dissolution Test

| Compound | % Zein Dissolved in $H_2O$ |
| --- | --- |
| Blank (control) | 9% |
| sodium dodecylsulfate (SDS) | 86% |
| Sodium laurylisethionate (SLI) (sulfonate) | 55% |
| Sodium lauryl sulfooxybutyrate (LSB) | 54% |
| Sodium decyl sulfooxybutyrate (DSB) | 54% |

As shown by the comparison of LSB and DSB, the dissolution of Zein appears to be independent of the hydrophobe chain length.

EXAMPLE 13

Sulfoxy Mono- or Di-Ester is Used in a Toilet Soap Bar

| Ingredients | % by Weight |
| --- | --- |
| C8-24 fatty acid soap | 30%–95% |
| Alkyl sulfooxy alkanoate | 0–45% |
| Alkyl sulfate | 0–5% |
| Moisturizer (e.g. Sorbitol or Glycerin) | 0.1–10% |
| Water soluble polymer (e.g. Cellulase or Polyacrylates) | 0–10% |
| Sequestering agents (e.g. citrate) | 0.1–0.5% |
| Dye stuff | <0.1% |
| Optical brighteners | <0.1% |
| Whitening agents | 0.1–0.4% |
| Fragrance | 0.1–2.0% |
| Water | Balance |

EXAMPLE 14

Sulfate Ester is Used in a Facial/Body Cleanser Composition

| Ingredients | % by Weight |
| --- | --- |
| C8-24 fatty acid salt (e.g. triethanolamine) | 1–45% |
| Alkyl sulfooxy alkanoate | 10–75% |
| Alkyl sulfate | 0–20% |
| Coactive surfactant (e.g. cocoamidobetaine) | 1–15% |
| Moisturizer (e.g. sorbitol) | 0.1–15% |
| Refattying alcohol | 0.5–5% |
| Water soluble polymer | 0–10% |
| Thickener | 0–15% |
| Conditioner (e.g. quaternized cellulose) | 0–0.5% |
| Sequestering agents (e.g. citrate) | 0.1–0.4% |
| Dye stuff | <0.1% |
| Optical brighteners | <0.1% |
| Whitening agents | 0.1–0.4% |
| Fragrance | 0.1–3.0% |
| Preservatives | 0–0.2% |
| Water | Balance |

EXAMPLE 15

Sulfate Ester is Used in a Toothpaste Composition

| Ingredients | % by Weight |
| --- | --- |
| Synthetic surfactants (sodium lauryl sulfate) | 1.5% |
| Alkyl sulfooxy alkanoate | 0–10% |
| Alkyl sulfate | 0–1% |
| Abrasive (e.g. silic acid/$CaCO_3$) | 20–55% |
| Active ingredients (e.g., | 0.1–2% |

| Ingredients | % by Weight |
| --- | --- |
| Pyrophosphates) | |
| Humectant (glycerin, sorbitol) | 10–45% |
| Thickeners (cellulose derivatives) | 0–3% |
| Sequestering agents (e.g. citrate) | 0.1–04% |
| Flavoring agents | 0.5–2% |
| Sweeteners | <0.5% |
| Dye stuff | <0.1% |
| Water | Balance |

I claim:

1. A personal product composition selected from the group consisting of soap bar compositions, facial or body cleansing compositions, shampoo compositions, conditioner compositions, cosmetic compositions, dental compositions and underarm deodorant/anti-perspirant compositions wherein said compositions contain an alkyl sulfooxy alkanoate molecule having the formula

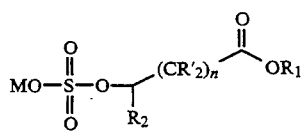

wherein:

M is selected from the group consisting of an alkali-metal, an alkaline earth metal, a cationic amino acid and salt forming cations;

R' is hydrogen;

$R_2$ is hydrogen or $CH_3$;

$R_1$ is a straight chain carbon having 12 or more carbons;

$n \leqq 0$; and while molecule is capable of forming a hydroxy carboxylic acid ester, a hydroxy carboxylic acid, a sulfooxy carboxylate and/or alcohol when the surfactant is metabolized or hydrolyzed.

2. A composition according to claim 1, wherein $R_1$ is $C_{12}H_{25}$ and $R_2$ is $CH_3$(LSP).

3. A composition according to claim 1, which is a soap bar composition and which has the following components:

| Ingredients | % by Weight |
| --- | --- |
| C8-24 fatty acid soap | 30–95% |
| Alkyl sulfooxy alkanoate | 0–45% |
| Alkyl sulfate | 0–5% |
| Moisturizer | 0.1–10% |
| Water soluble polymer | 0–10% |
| Sequestering agents | 0.1–0.5% |
| Dye stuff | <0.1% |
| Optical brighteners | <0.1% |
| Whitening agents | 0.1–0.4% |
| Fragrance | 0.1–2.0% |
| Water | Balance. |

4. A composition according to claim 3 wherein, in the alkyl sulfooxy alkanoate compound, $R_1$ is $C_{12}H_{25}$ and $R_2$ is $CH_3$.

* * * * *